US012678780B2

(12) United States Patent
Hashimoto et al.

(10) Patent No.: US 12,678,780 B2
(45) Date of Patent: *Jul. 14, 2026

(54) TESTING SYSTEM

(71) Applicant: KAWASAKI JUKOGYO KABUSHIKI KAISHA, Kobe (JP)

(72) Inventors: Yasuhiko Hashimoto, Kobe (JP); Yukio Iwasaki, Kobe (JP); Atsushi Kameyama, Kakogawa (JP); Toshihiko Miyazaki, Kobe (JP); Shogo Kubota, Kobe (JP); Satoshi Ouchi, Kobe (JP); Eiji Mitsui, Kobe (JP); Tatsuya Shirai, Kakamigahara (JP); Hiroshi Mitsui, Kakamigahara (JP); Tomoya Nakanishi, Kakamigahara (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 671 days.

This patent is subject to a terminal disclaimer.

(21) Appl. No.: 18/000,560

(22) PCT Filed: Jun. 1, 2021

(86) PCT No.: PCT/JP2021/020882
§ 371 (c)(1),
(2) Date: Dec. 2, 2022

(87) PCT Pub. No.: WO2021/246410
PCT Pub. Date: Dec. 9, 2021

(65) Prior Publication Data
US 2023/0221344 A1     Jul. 13, 2023

(30) Foreign Application Priority Data

| | | |
|---|---|---|
| Jun. 2, 2020 | (JP) | 2020-096130 |
| Oct. 2, 2020 | (JP) | 2020-167769 |
| Jan. 14, 2021 | (JP) | 2021-004272 |

(51) Int. Cl.
| | |
|---|---|
| *G01N 35/04* | (2006.01) |
| *A61B 10/00* | (2006.01) |
(Continued)

(52) U.S. Cl.
CPC ............ *B01L 1/52* (2019.08); *A61B 10/0051* (2013.01); *A61G 10/00* (2013.01); *A61G 10/005* (2013.01);
(Continued)

(58) Field of Classification Search
CPC .... B01L 1/52; B01L 1/025; B01L 1/04; B01L 3/502; B01L 2200/025; B01L 2300/042;
(Continued)

(56) References Cited

U.S. PATENT DOCUMENTS

| | | | |
|---|---|---|---|
| 2004/0022682 A1 | 2/2004 | Itoh | |
| 2006/0257999 A1* | 11/2006 | Chang | C40B 60/06 435/289.1 |
(Continued)

FOREIGN PATENT DOCUMENTS

| | | | |
|---|---|---|---|
| CN | 201096778 Y | * | 8/2008 |
| CN | 109184268 A | | 1/2019 |
(Continued)

*Primary Examiner* — Benjamin R Whatley
(74) *Attorney, Agent, or Firm* — METROLEX IP LAW GROUP, PLLC; Robert L. Scott, Esq.

(57) ABSTRACT

A testing system collects a specimen from a subject and measures the collected specimen to test the specimen, and includes a first unit to collect and receive the specimen, a second unit to be connected to the first unit and to preprocess the specimen before measurement, a third unit to be connected to the second unit and to measure the preprocessed specimen, and a robot provided in at least one of the first unit, the second unit, or the third unit to process the specimen.

18 Claims, 22 Drawing Sheets

/1100
/1005

| FIRST UNIT /1001 | SECOND UNIT /1002 | THIRD UNIT /1003 |
|---|---|---|
| 1004 ROBOT | 1004 ROBOT | 1004 ROBOT |

1006a         1006b

(51) Int. Cl.

| | |
|---|---|
| *A61G 10/00* | (2006.01) |
| *A61L 2/10* | (2006.01) |
| *A61L 2/26* | (2006.01) |
| *B01L 1/00* | (2006.01) |
| *B01L 1/02* | (2006.01) |
| *B01L 1/04* | (2006.01) |
| *B01L 3/00* | (2006.01) |
| *B25J 19/02* | (2006.01) |
| *G01N 35/00* | (2006.01) |
| *G01N 35/10* | (2006.01) |
| *B25J 21/00* | (2006.01) |

(52) U.S. Cl.
  CPC .................................... *A61L 2/10* (2013.01);
      *A61L 2/26* (2013.01); *B01L 1/025* (2013.01);
      *B01L 1/04* (2013.01); *B01L 3/502* (2013.01);
      *B25J 19/02* (2013.01); *G01N 35/00* (2013.01);
      *G01N 35/0099* (2013.01); *G01N 35/04*
      (2013.01); *G01N 35/1002* (2013.01); *A61L*
      *2202/11* (2013.01); *B01L 2200/025* (2013.01);
      *B01L 2300/042* (2013.01); *B01L 2300/046*
      (2013.01); *B01L 2300/0609* (2013.01); *B01L*
      *2300/0829* (2013.01); *B25J 21/00* (2013.01);
      *G01N 2035/00306* (2013.01); *G01N*
      *2035/00326* (2013.01)

(58) Field of Classification Search
  CPC ....... B01L 2300/046; B01L 2300/0609; B01L
      2300/0829; A61B 10/0051; A61G 10/00;
      A61G 10/005; A61L 2/10; A61L 2/26;
      A61L 2202/11; B25J 19/02; B25J 21/00;
      B25J 9/0084; B25J 9/0087; G01N 35/00;
      G01N 35/0099; G01N 35/04; G01N
      35/1002; G01N 2035/00306; G01N
      2035/00326; E04H 3/08
  See application file for complete search history.

(56) References Cited

U.S. PATENT DOCUMENTS

| | | | |
|---|---|---|---|
| 2009/0047179 A1 | 2/2009 | Ping et al. | |
| 2009/0117620 A1* | 5/2009 | Fritchie ................. | B01L 3/5085 |
| | | | 422/68.1 |
| 2014/0137493 A1* | 5/2014 | Mouzannar ............... | E04H 3/08 |
| | | | 52/234 |
| 2016/0054340 A1* | 2/2016 | Gisler ................ | G01N 35/0092 |
| | | | 435/6.12 |
| 2017/0176481 A1* | 6/2017 | Accurso .......... | G01N 35/00029 |
| 2018/0045654 A1 | 2/2018 | Park et al. | |
| 2018/0298419 A1* | 10/2018 | Ronsick .................. | C12Q 1/24 |
| 2019/0302135 A1 | 10/2019 | Yoshida et al. | |
| 2023/0221344 A1 | 7/2023 | Hashimoto et al. | |

FOREIGN PATENT DOCUMENTS

| | | | | |
|---|---|---|---|---|
| CN | 110982685 A | * | 4/2020 | ........... C12M 41/36 |
| EP | 0 973 039 A2 | | 1/2000 | |
| JP | H4-333782 A | | 11/1992 | |
| JP | 2018-511787 A | | 4/2018 | |
| JP | 2019-174369 A | | 10/2019 | |
| WO | 2021/246410 A1 | | 12/2021 | |

* cited by examiner

SPECIMEN
WASH SOLUTION A
WASH SOLUTION B

ELUATE (WATER)

SPECIMEN
WASH SOLUTION A
WASH SOLUTION B

ELUATE (WATER)

1007b
1073

1292
1029
1291

TESTING SYSTEM

TECHNICAL FIELD

The present disclosure relates to a testing system.

BACKGROUND ART

Japanese Patent Laid-Open No. 4-333782 discloses a unit hospital to address urgent placement and expansion of a medical facility. The unit hospital includes a unit in which a bio-clean room is made up of transportable modules. The unit disclosed in Japanese Patent Laid-Open No. 4-333782 is detachably connected to a facility module formed by connecting other portable modules.

PRIOR ART

Patent Document

Patent Document 1: Japanese Patent Laid-Open No. 4-333782

SUMMARY OF THE INVENTION

Problems to be Solved by the Invention

COVID-19 pandemic has sharply increased the demand for testing for infectious viruses. A typical example of an infectious virus test is a polymerase chain reaction (PCR) test. In the PCR test, first, a specimen is collected from a subject into a specimen container. Then, the specimen container is transported to a PCR testing facility. The specimen in the specimen container is transferred to a container for testing. A virus-derived nucleic acid is extracted in the container, and the nucleic acid is amplified by PCR to diagnose whether the subject is positive or negative for virus infection. Furthermore, in the PCR test, the specimen is collected and preprocessed by a testing operator. Therefore, when a PCR test is performed by a testing operator using a conventional unit hospital as disclosed in Japanese Patent Laid-Open No. 4-333782, work mistakes may occur due to human errors especially in a situation in which the number of specimens increases and the testing operator continues to work alone for a long time. Furthermore, the testing operator handles infectious specimens, and thus the risk of infection is increased.

The present disclosure is intended to solve the above problems. The present disclosure aims to provide a testing system capable of reducing or preventing human errors and capable of reducing the risk of infection of a testing operator.

Means for Solving the Problems

A testing system according to one aspect of the present disclosure collects a specimen from a subject and measures the collected specimen to test the specimen, and includes a first unit to collect and receive the specimen, a second unit to be connected to the first unit and to preprocess the specimen before measurement, a third unit to be connected to the second unit and to measure the preprocessed specimen, and a robot provided in at least one of the first unit, the second unit, or the third unit to process the specimen.

According to the present disclosure, as described above, the robot is provided to process the specimen such that the robot can perform the work to be performed by a testing operator instead of the testing operator, and thus the work burden on the testing operator can be reduced. Furthermore, even when the specimen is infectious, the work of the testing operator is reduced, and thus the risk of infection can be reduced or prevented. Consequently, it is possible to provide the testing system capable of reducing or preventing human errors and capable of reducing the risk of infection of the testing operator.

MODES FOR CARRYING OUT THE INVENTION

Figure 1:
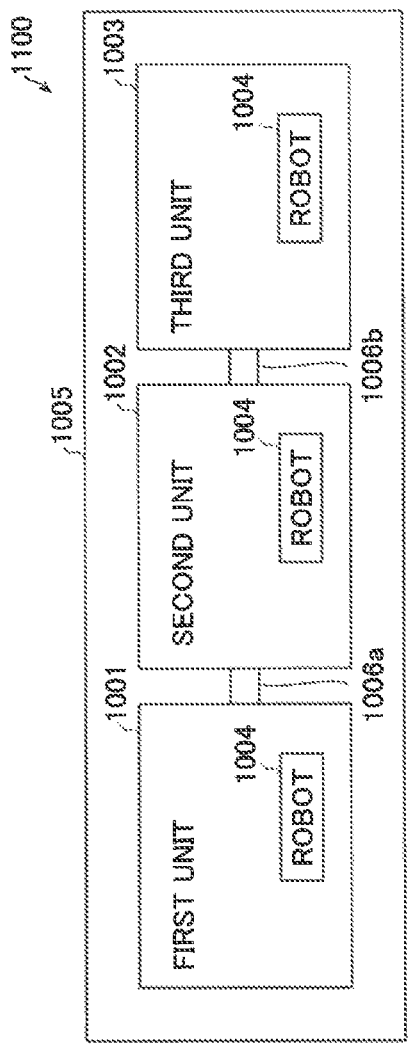
FIG. 1 is a diagram schematically showing the overall structure of a testing system according to a first embodiment.

Embodiments of the present disclosure are hereinafter described with reference to the drawings. The embodiments described below illustrate comprehensive or concrete examples. Furthermore, components that are not described in the independent claim indicating the top concept among components in the following embodiments are described as arbitrary components. Each figure in the accompanying drawings is a schematic figure, and is not necessarily illustrated exactly. In each drawing, the same reference numerals are assigned to substantially the same components, and thus redundant explanation may be omitted or simplified. The term "device (apparatus)" as used in this specification and the claims may not only indicate a sole device (apparatus), but may also indicate a system including a plurality of devices (apparatuses).

First Embodiment

A testing system 1100 according to a first embodiment is now described with reference to FIGS. 1 to 12. The testing system 1100 according to the first embodiment collects a specimen from a subject and measures the collected specimen to test the specimen. For example, the testing system 1100 is for performing RT-PCR tests for infectious viruses. The infectious viruses are not particularly limited, but an example of the infectious viruses is COVID-19.

Figure 2:
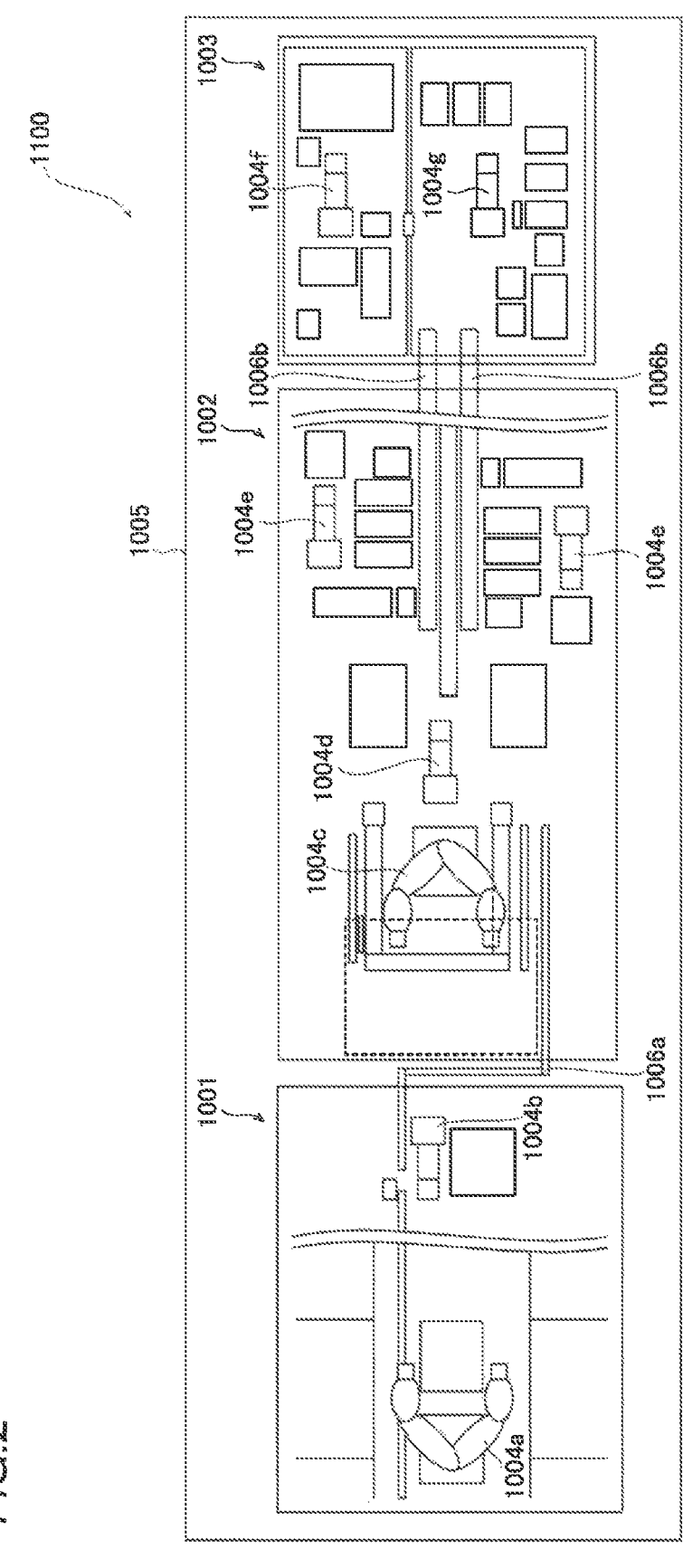
FIG. 2 is a diagram showing the specific overall structure of the testing system according to the first embodiment.

As shown in FIGS. 1 and 2, the testing system 1100 includes a first unit 1001, a second unit 1002, and a third unit 1003. A robot 1004 is provided in each of the first unit 1001, the second unit 1002, and the third unit 1003 of the testing system 1100. The first unit 1001, the second unit 1002, and the third unit 1003 are provided inside a container 1005. At least one of the first unit 1001, the second unit 1002, or the third unit 1003 may be provided inside the container 1005. Thus, the testing system 1100 can be easily transported and installed.

The testing system 1100 also includes conveyance sections 1006a and 1006b that connect the first unit 1001, the second unit 1002, and the third unit 1003 to each other. Specifically, the first unit 1001 and the second unit 1002 are connected to each other by the conveyance section 1006a. The second unit 1002 and the third unit 1003 are connected to each other by the conveyance section 1006b. Thus, it is possible to easily move the specimen between the first unit 1001, the second unit 1002, and the third unit 1003 by the conveyance sections 1006a and 1006b.

The first unit 1001 collects and receives the specimen. For example, in the first unit 1001, the specimen is collected from the subject, and the collected specimen is diluted with a dilute solution. In the first unit 1001, the diluted specimen is agitated. In the first unit 1001, the diluted specimen is centrifuged. The second unit 1002 is connected to the first unit 1001 and preprocesses the specimen before measurement. For example, in the second unit 1002, an inactivation process is performed as preprocessing of the specimen. Furthermore, in the second unit 1002, a nucleic acid extraction process is performed as preprocessing of the specimen. The third unit 1003 is connected to the second unit 1002 and measures the preprocessed specimen. For example, in the third unit 1003, a process is performed to measure whether or not the specimen contains an infectious virus by an RT-PCR test.

The robot 1004 provided in each of the first unit 1001, the second unit 1002, and the third unit 1003 of the testing system 1100 processes the specimen. For example, the robot 1004 transports, opens, and closes a container containing the specimen. The robot 1004 also dispenses the specimen and a reagent. The robot 1004 also transports objects such as a container, a reagent, and a pallet required for processing. The robot 1004 may be provided in at least one of the first unit 1001, the second unit 1002, or the third unit 1003.

The testing system 1100 is placed at a moving base for getting on and off a mobile body. For example, the testing system 1100 is placed at an airport, a station, a bus terminal, or a ferry terminal corresponding to the moving base. The mobile body is an aircraft, a train, a bus, or a marine vessel, for example. Thus, a test for an infectious disease can be performed at the moving base by the testing system 1100, and thus it is possible to immediately confirm whether the test for the infectious disease is positive or negative at the moving base. Consequently, it is possible to effectively reduce or prevent the spread of the infectious disease from the moving base.

An example in which the testing system 1100 is placed at an airport is described. At the airport, there are a terminal building, a railroad and bus station, a taxi stand, a parking lot, etc. Passengers of aircraft come and go between each of the station, the taxi stand, and the parking lot and an entrance and exit of the terminal building.

The terminal building includes the entrance and exit, a check-in counter for boarding procedures, a security checkpoint using X-ray inspection and metal detectors or the like, a boarding waiting area, a boarding gate, a baggage claim, and an arrival gate. Passengers of aircraft departing from the airport proceed through the check-in counter, the security checkpoint, the boarding waiting area, and the boarding gate in this order. Passengers of aircraft arriving at the airport proceed through the baggage claim and the arrival gate in this order.

The testing system 1100 is placed at at least one of the entrance and exit, the check-in counter, or the security checkpoint. Thus, it is possible to reduce or prevent passing of untested passengers through the security checkpoint. Furthermore, the testing system 1100 may be placed at at least one of the baggage claim or the arrival gate. Thus, it is possible to reduce or prevent passing of untested passengers through the arrival gate.

When there are a plurality of terminal buildings at the airport, the testing system 1100 may be placed at the above locations for each terminal building. The testing system 1100 may be placed not only in the terminal building, but also at the station, the taxi stand, and the parking lot.

Figure 3:
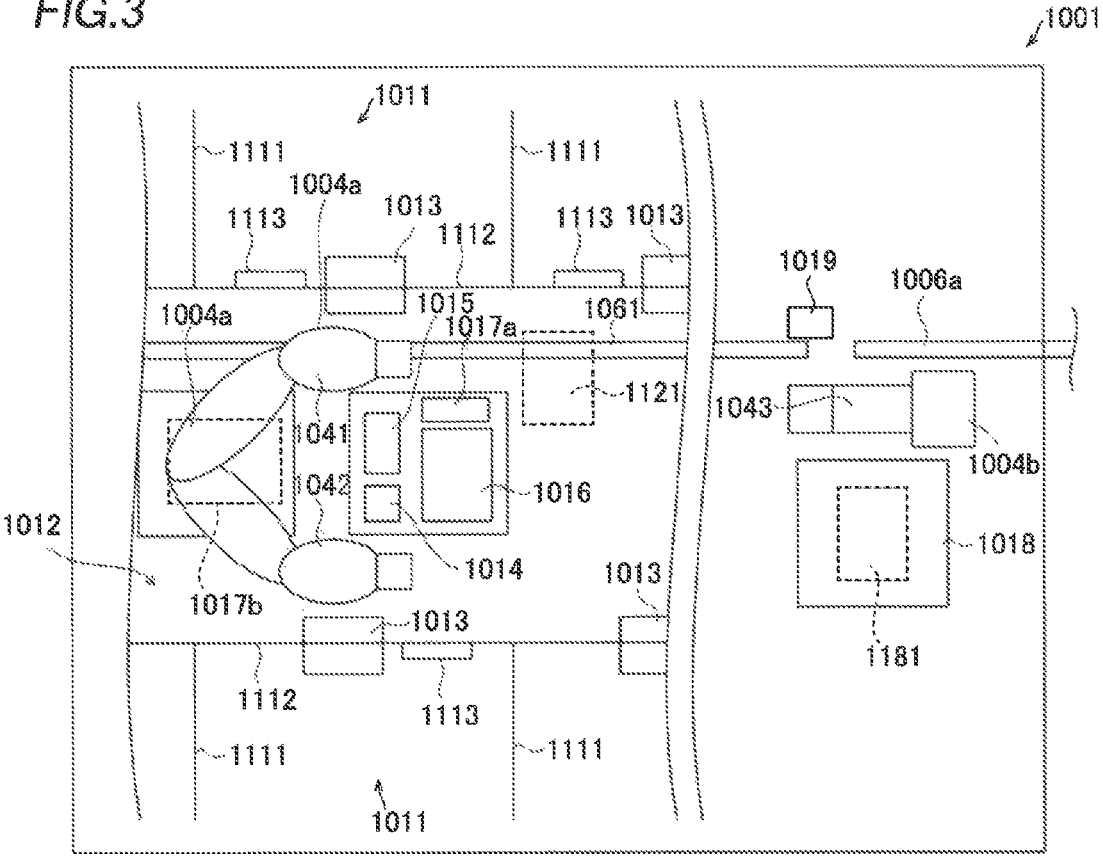
FIG. 3 is a diagram showing the structure of a first unit of the testing system according to the first embodiment.

The first unit 1001 collects and receives a saliva or nasal specimen. As shown in FIG. 3, the first unit 1001 includes a first robot 1004a as the robot 1004 for processing the specimen. The first robot 1004a includes robot arms 1041 and 1042. That is, the first robot 1004a performs processing using the two robot arms. The robot arms 1041 and 1042 each include a horizontal joint and an elevating mechanism connected to the horizontal joint. The horizontal joint moves the tip end of the robot arm 1041 (1042) in a horizontal direction. The elevating mechanism moves the tip end of the robot arm 1041 (1042) in an upward-downward direction (height direction).

The first unit 1001 includes a subject area 1011 in which a subject is placed. The first unit 1001 includes a robot area 1012 that is partitioned from the subject area 1011 and in which the first robot 1004a for processing the specimen is placed.

As shown in FIG. 3, the subject area 1011 is partitioned into a plurality of booths by partitions 1111. Thus, it is possible to reduce or prevent infection between a plurality of subjects. The subject area 1011 and the robot area 1012 are partitioned from each other by partitions 1112. Thus, it is possible to reduce or prevent entry of the subject into the robot area 1012.

The first unit 1001 includes a scale 1014 to weigh the collected specimen. The first unit 1001 adjusts the amount of dilute solution according to the amount of specimen weighed by the scale 1014 to dilute the specimen. That is, when the amount of specimen is small, the amount of dilute solution is decreased to dilute the specimen, and when the amount of specimen is large, the amount of dilute solution is increased to dilute the specimen. Thus, the specimen can be diluted to an appropriate range of concentrations. The first unit 1001 may dilute the collected specimen with a dilute solution containing an inactivating component that inactivates the virus. Thus, the inactivation process can be performed along with the dilution of the specimen.

The first unit 1001 includes a dilute solution supplier 1016 to supply the dilute solution to dilute the specimen. The dilute solution supplier 1016 supplies the dilute solution to a specimen collection container 1007a grasped by the first robot 1004a.

The first unit 1001 includes a notifier 1113 to notify the subject of re-collection of the specimen when the amount of specimen weighed by the scale 1014 is insufficient. The notifier 1113 is provided in the subject area 1011, for example. The notifier 1113 is a display that displays an image, for example. The notifier 1113 may be a speaker that outputs audio. Thus, it is possible to reduce or prevent incorrect testing due to an insufficient amount of specimen.

The first unit 1001 includes an ultraviolet irradiator 1017a. The first robot 1004a sterilizes the inside of the first unit 1001 with the ultraviolet irradiator 1017a. Specifically, the first robot 1004a grasps the ultraviolet irradiator 1017a while an ultraviolet lamp of the ultraviolet irradiator 1017a is lit, and irradiates the robot area 1012 of the first unit 1001 with ultraviolet rays to sterilize the robot area 1012. Thus, the first unit 1001 can be sterilized with ultraviolet rays, and thus contamination and infection can be effectively reduced or prevented.

Figure 4:
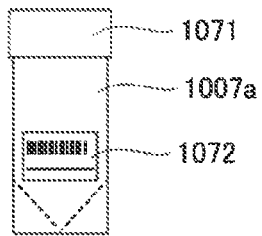
FIG. 4 is a diagram showing a specimen collection container of the testing system according to the first embodiment.

The first unit 1001 collects and receives the specimen in the specimen collection container 1007a to which an indication amount for specimen collection is attached, as shown in FIG. 4. Thus, the subject can easily know the amount of specimen to be delivered, and thus the specimen can be easily collected in just the right amount. The specimen collection container 1007a can be closed with a lid 1071. A label on which an identifier (a bar code, for example) containing information about the subject and an indication amount for specimen collection have been printed is attached to the specimen collection container 1007a.

Figure 5:
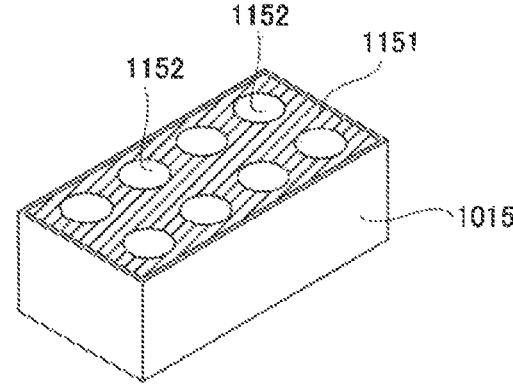
FIG. 5 is a diagram showing a disinfectant bath of the testing system according to the first embodiment.

As shown in FIG. 3, the first unit 1001 includes a disinfectant bath 1015 to disinfect the outer surface of the specimen collection container 1007a containing the collected specimen. As shown in FIG. 5, a sponge 1151 is arranged in the disinfectant bath 1015. The sponge 1151 is impregnated with a disinfectant (ethanol or hypochlorous acid water, for example). The sponge 1151 includes a plurality of holes 1152 into which the specimen collection container 1007a can be inserted. The specimen collection container 1007a is inserted into the hole 1152 of the sponge 1151 such that the outer surface of the specimen collection container 1007a is disinfected with the disinfectant. Thus, the outer surface of the specimen collection container 1007a can be disinfected, and thus contamination and infection can be effectively reduced or prevented.

Figure 6:
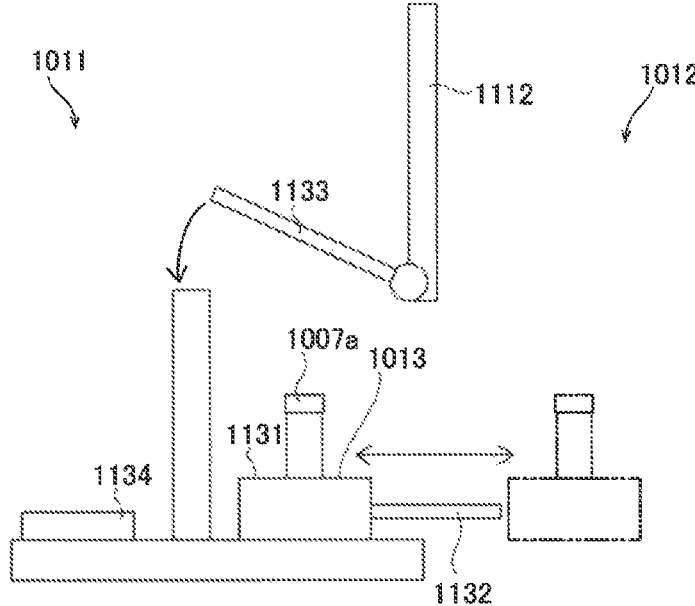
FIG. 6 is a diagram showing a specimen collection container conveyance section of the testing system according to the first embodiment.

As shown in FIG. 6, the first unit 1001 includes a specimen collection container conveyance section 1013 to transport the specimen collection container 1007a containing the collected specimen from the subject area 1011 to the robot area 1012. The specimen collection container conveyance section 1013 includes a placement section 1131 on which the specimen collection container 1007a is placed, and an air cylinder 1132 driven by air pressure. The specimen collection container conveyance section 1013 moves the placement section 1131 by driving the air cylinder 1132 to transport the specimen collection container 1007a. The specimen collection container conveyance section 1013 may move the placement section 1131 from the subject area 1011 to the robot area 1012 based on a cover 1133 arranged in the subject area 1011 being closed. The cover 1133 is provided so as to be rotatable about a horizontal rotation axis. The cover 1133 can move between a closed position at which it rotates downward to cover the placement section 1131 and an open position at which it rotates upward to expose the placement section 1131. The placement section 1131 may be moved from the subject area 1011 to the robot area 1012 based on the cover 1133 being moved to the closed position. The specimen collection container conveyance section 1013 may move the placement section 1131 from the subject area 1011 to the robot area 1012 based on a switch 1134 arranged in the subject area 1011 being operated. The specimen collection container 1007a placed on the placement section 1131 moved to the robot area 1012 is grasped by the first robot 1004a and taken into the robot area 1012. Thus, the specimen can be easily moved from the subject area 1011 to the robot area 1012 while the subject area 1011 and the robot area 1012 are reliably isolated from each other.

As shown in FIG. 3, the first unit 1001 includes an air conditioner 1121 to adjust an air flow in the subject area 1011. The air conditioner 1121 creates a positive or negative pressure environment in the subject area 1011. Thus, the subject area 1011 can be kept clean.

The first unit 1001 includes a sterilizer 1017*b* to sterilize the first robot 1004*a* for processing the specimen. Thus, the first robot 1004*a* can be sterilized, and thus contamination and infection can be effectively reduced or prevented.

The first unit 1001 includes a conveyance section 1061 to transport the specimen collection container 1007*a* containing the specimen diluted with the dilute solution. The conveyance section 1061 transports the specimen collection container 1007*a* downstream toward a first robot 1004*b*.

The first unit 1001 includes a first centrifuge 1018 capable of centrifuging a plurality of specimens. The first unit 1001 drives the first centrifuge 1018 at predetermined time intervals to perform a centrifugal separation process on the specimens. In other words, even when the first centrifuge 1018 is not fully loaded with specimens, the centrifugal separation process is performed at the predetermined time intervals. Thus, it is possible to reduce or prevent delays in the process on the specimens due to waiting until the specimens are accumulated.

The first unit 1001 includes the first robot 1004*b* as the robot 1004 for processing the specimen. The first robot 1004*b* includes a vertical articulated robot arm 1043. The first robot 1004*b* transports the specimen collection container 1007*a* transported by the conveyance section 1061 to a shaker 1019, and transports it to the first centrifuge 1018 after the shaking process. Furthermore, the first robot 1004*b* transports the specimen collection container 1007*a* to the conveyance section 1006*a* after the centrifugal separation process.

In the first unit 1001, a balance centrifuge tube is installed in the first centrifuge 1018 by the first robot 1004*b*, and the first centrifuge 1018 is driven to perform the centrifugal separation process on the specimen. Thus, even when the number of specimen collection containers 1007*a* to be subjected to the centrifugal separation process differs each time due to the centrifugal separation process performed at the predetermined time intervals, the balance can be adjusted by the balance centrifuge tube.

The first unit 1001 includes an imager 1181 to capture an image for acquiring the position of the specimen inside the first centrifuge 1018. The first unit 1001 takes out the specimen (specimen collection container 1007*a*) from the first centrifuge 1018 with the first robot 1004*b* for processing the specimen. Specifically, the first unit 1001 recognizes the position of the specimen collection container 1007*a* in the first centrifuge 1018 based on the image captured by the imager 1181. Then, the first unit 1001 takes out the specimen collection container 1007*a* at the recognized position with the first robot 1004*b*. Thus, the specimen collection container 1007*a* can be easily taken out from the first centrifuge 1018 by the first robot 1004*b*.

When the specimen is retested, the first unit 1001 receives the specimen to be retested from the second unit 1002, and subjects the received specimen to be retested to the centrifugal separation process by the first centrifuge 1018. Thus, the specimen can be retested without re-collecting a specimen.

The first unit 1001 includes the shaker 1019 to shake the specimen. A plurality of specimen collection containers 1007*a* can be placed on the shaker 1019. The shaker 1019 is used to agitate the specimen in the placed specimen collection container 1007*a*. Furthermore, the shaker 1019 periodically moves and shakes the placed specimen collection container 1007*a*. The shaker 1019 stops at a certain position after the shaking process is completed. Thus, the first robot

1004*b* can go to the position at which the specimen collection container 1007*a* is placed on the shaker 1019 to pick up the shaken specimen collection container 1007*a*, and thus the specimen collection container 1007*a* can be easily taken out from the shaker 1019 by the first robot 1004*b*.

Figure 7:
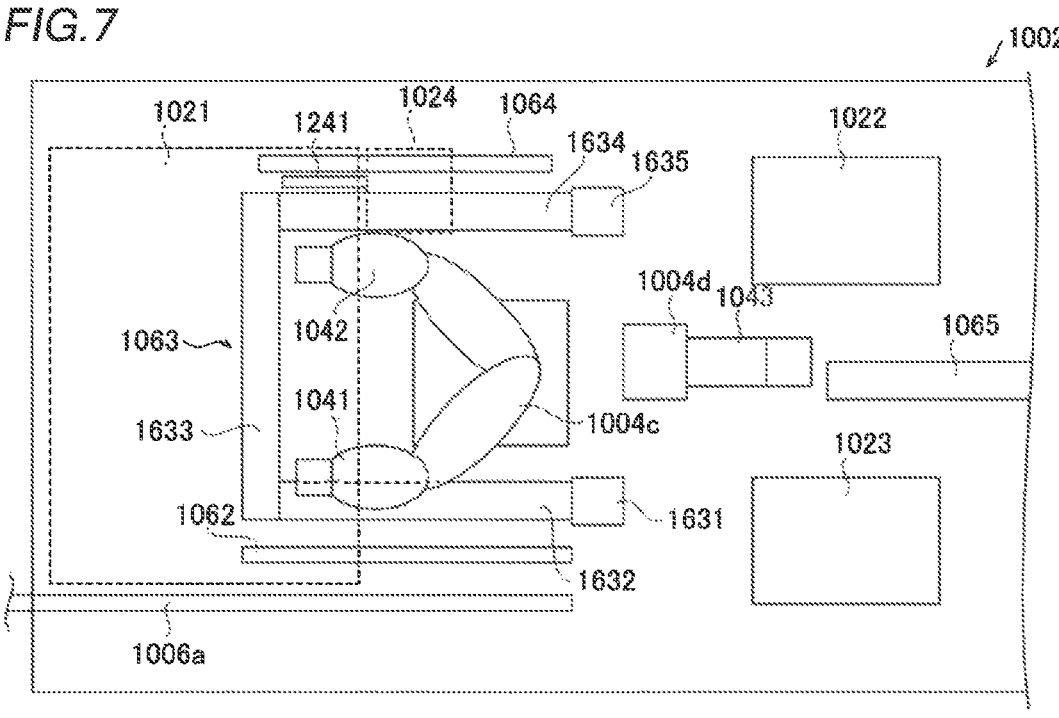
FIG. 7 is a diagram showing a structure for performing an opening-dispensing process and an inactivation process in a second unit of the testing system according to the first embodiment.
Figure 9:
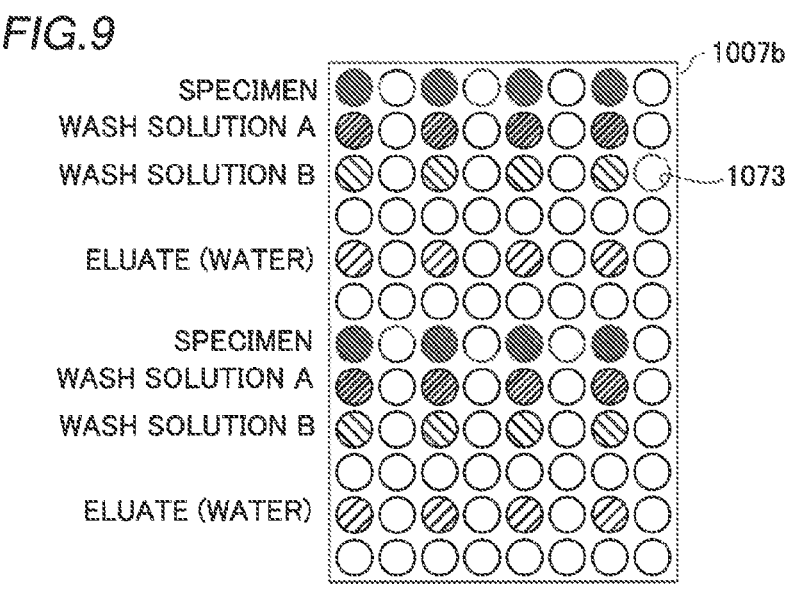
FIG. 9 is a diagram showing a plate for the nucleic acid extraction process of the testing system according to the first embodiment.

As shown in FIG. 7, the second unit 1002 includes a second robot 1004*c* as the robot 1004 that dispenses the diluted specimen onto a plate 1007*b* including a plurality of wells 1073. As shown in FIG. 9, the plate 1007*b* has 96 deep wells in 8 rows and 12 columns, for example. The second robot 1004*c* includes robot arms 1041 and 1042 with horizontal joints.

The second unit 1002 includes a third robot 1004*d* as the robot 1004 that supplies the plate 1007*b* to a dispensing position. The third robot 1004*d* includes a vertical articulated robot arm 1043. The third robot 1004*d* grasps the empty plate 1007*b* supplied from a feeder 1023 and transports it to a supply table 1631. Furthermore, the third robot 1004*d* moves the specimen collection container 1007*a* transported by the conveyance section 1006*a* to a conveyance section 1062. The third robot 1004*d* transports a tip rack supplied from the feeder 1023 to a tip supply slider 1064. Furthermore, the third robot 1004*d* transports the specimen collection container 1007*a* from which a portion of the contained specimen has been dispensed onto the plate 1007*b* from the conveyance section 1062 to a storage rack 1022. Moreover, the third robot 1004*d* transports the plate 1007*b* discharged from a discharge table 1635 to a conveyance section 1065.

The second robot 1004*c* dispenses the specimen from the specimen collection container 1007*a* transported by the conveyance section 1062 onto the plate 1007*b*.

The second unit 1002 includes a plate conveyance section 1063 to transport the plate 1007*b* over a predetermined period of time to inactivate the specimen on the plate. The plate conveyance section 1063 includes a conveyance section 1632, a conveyance section 1633, and a conveyance section 1634. The conveyance sections 1632, 1633, and 1634 of the plate conveyance section 1063 are arranged in a substantially U shape so as to surround the second robot 1004*c*.

The conveyance section 1632 transports the plate 1007*b* from the supply table 1631 to the conveyance section 1633. In the supply table 1631, an inactivation liquid, a wash solution A, a wash solution B, and an eluate (water) are supplied to the plate 1007*b*. In the conveyance section 1633, the specimen is dispensed from the specimen collection container 1007*a* onto the plate 1007*b*. Then, the conveyance section 1633 transports the plate 1007*b* to the conveyance section 1634 over a period of time (10 minutes, for example) necessary for inactivation. The conveyance section 1634 transports the plate 1007*b* to the discharge table 1635. Thus, the inactivation process can be performed on a plurality of plates 1007*b* concurrently.

The second unit 1002 includes the storage rack 1022 to store, for a predetermined period of time, the specimen collection container 1007*a* containing the collected specimen, from which a portion of the specimen has been dispensed onto the plate 1007*b* and in which a remaining portion of the specimen has been contained. The storage rack 1022 stores the specimen collection container 1007*a* for two hours, for example. Thus, when retesting is required, the specimen can be taken out from the storage rack 1022 and retested, and thus there is no need to re-collect a specimen.

The second unit 1002 includes a cabinet 1021 having an interior space in which the diluted specimen is dispensed onto the plate 1007*b* by the second robot 1004*c*. That is, the second robot 1004c is driven while moving a hand (end effector) within the interior space of the cabinet 1021. Thus, the specimen can be dispensed within the cabinet 1021, and thus an increase in the risk of infection due to diffusion of the specimen to the outside is effectively reduced or prevented.

The second unit 1002 includes a chute 1241 to discard a tip for dispensing the diluted specimen. The tip discarded in the chute 1241 is moved to a disposal box 1024 and stored therein. Thus, the used tip can be easily discarded.

The second unit 1002 dispenses a plurality of diluted specimens into a plurality of wells 1073 of the plate 1007b with empty wells 1073 interposed therebetween, as shown in FIG. 9. Thus, the specimen can be dispensed at intervals, and thus contamination can be effectively reduced or prevented.

Figure 8:
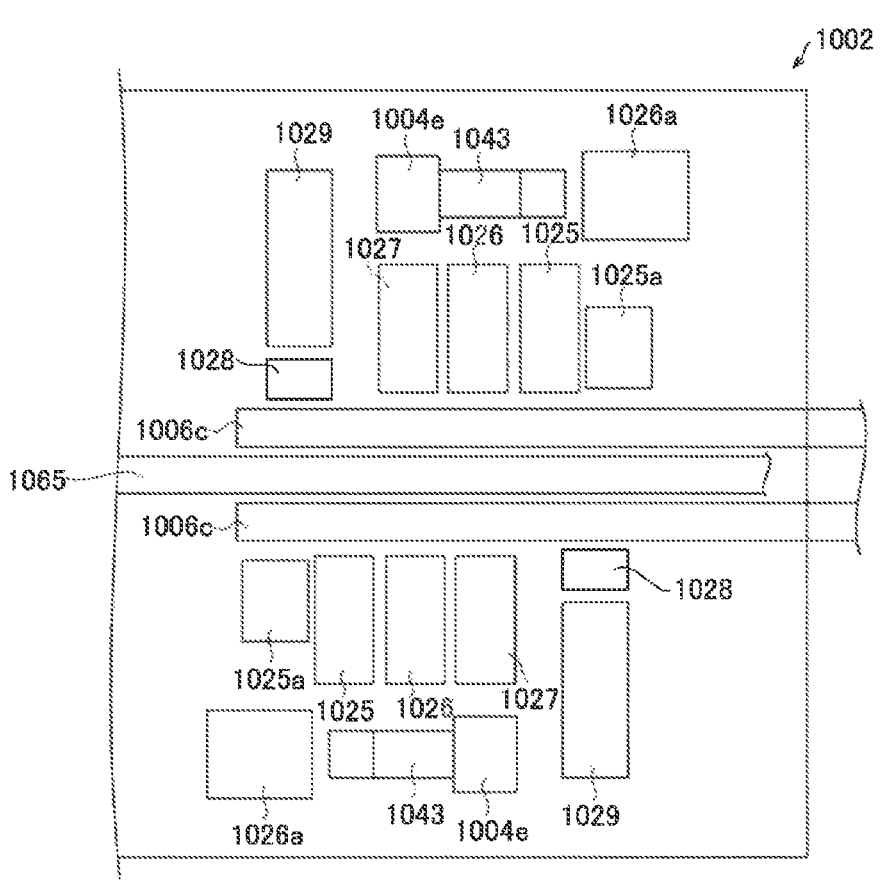
FIG. 8 is a diagram showing a structure for performing a nucleic acid extraction process in the second unit of the testing system according to the first embodiment.

As shown in FIG. 8, the second unit 1002 includes a plurality of robots 1004e as the robots 1004 that perform the nucleic acid extraction process. The robots 1004e include vertical articulated robot arms 1043. In the nucleic acid extraction process, the conveyance section 1065 transports the plate 1007b. The plate 1007b transported by the conveyance section 1065 is moved to a workbench by the robot 1004e and subjected to the nucleic acid extraction process. The second unit 1002 includes magnet portions 1025, tip rack place 1026, heaters 1027, shakers 1028, and disposal boxes 1029. The second unit 1002 also includes magnetic particle suppliers 1025a and tip rack places 1026a.

The magnet portions 1025 are used to collect magnetic particles supplied from the magnetic particle suppliers 1025a to the specimen on the plate 1007b. Specifically, the magnet portions 1025 collect magnetism by causing magnets to act on the specimen on the plate 1007b in a state in which the plate 1007b is placed on the magnet portions 1025.

In the tip rack places 1026, tip racks supplied from the tip rack places 1026a are placed. The used tip racks are returned to the tip rack places 1026a.

The heaters 1027 heat the specimen on the plate 1007b. The shakers 1028 shake and agitate the specimen on the plate 1007b.

Figure 10:
FIG. 10 is a diagram showing a disposal box of the second unit of the testing system according to the first embodiment.

In the disposal boxes 1029, the tip for dispensing the specimen and the plate 1007b are discarded. As shown in FIG. 10, the disposal boxes 1029 each include a storage 1291 and a tapered portion 1292. That is, the disposal boxes 1029 each have a tapered tip end (entrance). Thus, liquid splash can be reduced or prevented.

Figure 11:
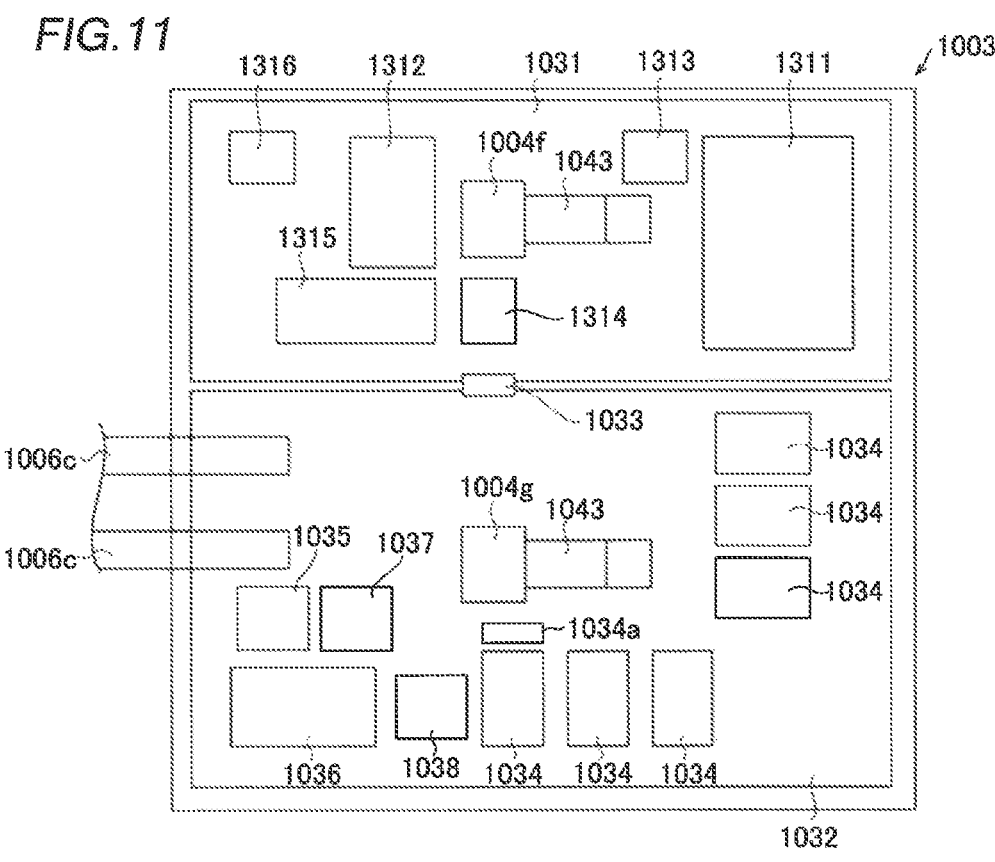
FIG. 11 is a diagram showing the structure of a third unit of the testing system according to the first embodiment.

As shown in FIG. 11, the third unit 1003 includes a reagent preparation room 1031 to prepare a reagent for measuring the specimen, and a measurement room 1032 to measure the specimen. The reagent preparation room 1031 is under a positive pressure. The measurement room 1032 is under a negative pressure. Thus, entry of floating foreign matter into the reagent preparation room 1031 is reduced or prevented. The outflow of the virus from the measurement room 1032 is reduced or prevented.

The third unit 1003 includes a shutter 1033 to open and close an opening that allows the reagent preparation room 1031 and the measurement room 1032 to communicate with each other. The shutter 1033 is opened when objects are exchanged between the reagent preparation room 1031 and the measurement room 1032, and otherwise closed. Thus, the specimen and the prepared reagent can be easily moved from the reagent preparation room 1031 to the measurement room 1032 while the reagent preparation room 1031 and the measurement room 1032 are reliably isolated from each other.

The third unit 1003 includes a robot 1004f as the robot 1004 that performs a reagent preparation process. The robot 1004f includes a vertical articulated robot arm 1043. In the reagent preparation room 1031 of the third unit 1003, a freezer 1311, a refrigerator 1312, an opening device 1313, a preparation place 1314, a tip place 1315, and a disposal box 1316 are provided.

The freezer 1311 stores a reagent (enzyme mixture) below freezing (e.g., −18° C.). The refrigerator 1312 stores a reagent (reaction mixture) at a low temperature (e.g., 4° C.). The reagent (enzyme mixture) and the reagent (reaction mixture) are mixed and prepared for use.

In other words, the third unit 1003 prepares a reagent in the reagent preparation room 1031 based on the testing reception status of the specimen. Thus, the reagent can be prepared in just the right amount.

The opening device 1313 opens a reagent container. At the preparation place 1314, the reagent (enzyme mixture) and a reagent (reaction mixture) are mixed and prepared.

The third unit 1003 includes a fourth robot 1004g as the robot 1004 that performs a process to supply the specimen to specimen measurement units 1034. The fourth robot 1004g includes a vertical articulated robot arm 1043. The measurement room 1032 of the third unit 1003 includes a plurality of specimen measurement units 1034, a second centrifuge 1035, a tube holder 1036, a lid closer 1037, and a disposal box 1038.

Figure 12:
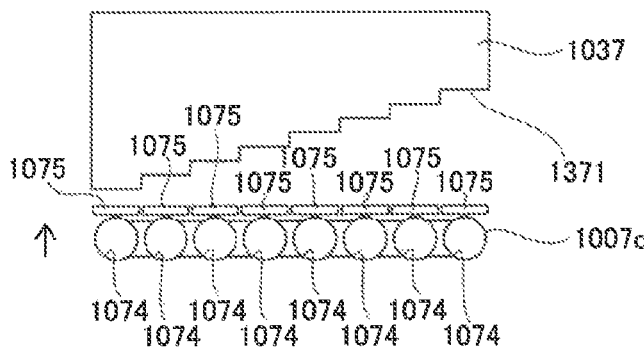
FIG. 12 is a diagram showing a lid closing member of the testing system according to the first embodiment.

The specimen measurement units 1034 measure the specimen while the specimen is accommodated in a multiple-connected tube 1007c including a row of tubes 1074 in which a plurality of specimens can be accommodated. The specimen measurement units 1034 perform measurement by RT-PCR, for example. As shown in FIG. 12, the multiple-connected tube 1007c is formed by connecting eight tubes 1074 in a straight line, for example. A lid 1075 is connected to each of the tubes 1074 of the multiple-connected tube 1007c. The lid 1075 closes the tube 1074 by bending the connecting portion.

The third unit 1003 includes an open state detector 1034a to detect that the lid 1075 of the multiple-connected tube 1007c is open. Thus, handling of the multiple-connected tube 1007c despite the open lid 1075 of the multiple-connected tube 1007c is reduced or prevented, and thus contamination due to the open lid 1075 of the multiple-connected tube 1007c can be effectively reduced or prevented.

The second centrifuge 1035 centrifuges the specimen. After the centrifugal separation process is completed, a stop position of the second centrifuge 1035 is aligned, and the second centrifuge 1035 is stopped at the stop position. Thus, the fourth robot 1004g only needs to go to the aligned stop position and pick up the centrifuged specimen, and thus the centrifuged specimen can be easily taken out from the second centrifuge 1035 by the fourth robot 1004g.

The tube holder 1036 holds a plurality of multiple-connected tubes 1007c. Specifically, the tube holder 1036 holds the multiple-connected tubes 1007c stacked in the upward-downward direction.

The fourth robot 1004g transports the multiple-connected tube 1007c. In the third unit 1003, the fourth robot 1004g takes out the multiple-connected tube 1007c downward from the tube holder 1036, dispenses the specimen into the multiple-connected tube 1007c, and then performs a process to close the lids 1075 respectively connected to the plurality of tubes 1074 while bending them at different timings.

Specifically, as shown in FIG. 12, in the lid closer 1037, the positions of a plurality of contact portions 1371 that the plurality of lids 1075 of the multiple-connected tube 1007c respectively contact are stepped in a plan view. Thus, the timings at which the plurality of lids 1075 of the multiple-connected tube 1007c contact the contact portions 1371 are different from each other. Consequently, the plurality of lids 1075 of the multiple-connected tube 1007c can be easily closed.

The third unit 1003 measures a control reagent for controlling testing accuracy at a predetermined timing. Thus, a decrease in testing accuracy can be effectively reduced or prevented.

In the first embodiment, as described above, the robot 1004 for processing the specimen is provided such that the robot 1004 can perform the work to be performed by a testing operator instead of the testing operator, and thus the work burden on the testing operator can be reduced. Furthermore, even when the specimen is infectious, the work of the testing operator is reduced, and thus the risk of infection can be reduced or prevented. Consequently, it is possible to provide the testing system 1100 capable of reducing or preventing human errors and capable of reducing the risk of infection of the testing operator.

Second Embodiment

A testing system 1200 according to a second embodiment is now described with reference to FIG. 13.

Figure 13:
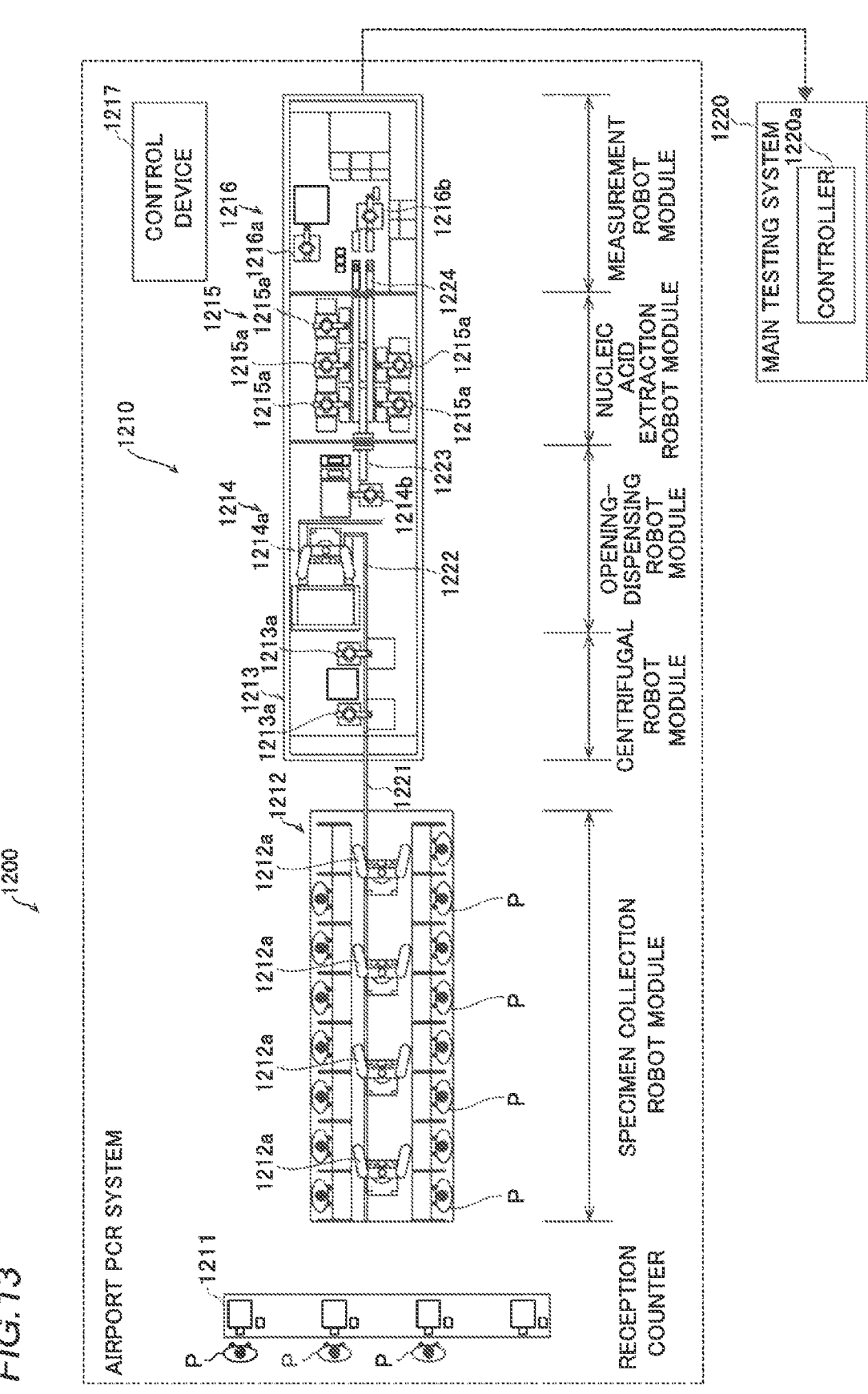
FIG. 13 is a diagram showing the specific overall structure of a testing system according to a second embodiment.

As shown in FIG. 13, the testing system 1200 includes an airport PCR system 1210 and a main testing system 1220.

The airport PCR system 1210 includes a reception counter 1211, a specimen collection robot module 1212, a centrifugal robot module 1213, an opening-dispensing robot module 1214, a nucleic acid extraction robot module 1215, a measurement robot module 1216, and a control device 1217.

The reception counter 1211 supplies a specimen container to a subject P. The reception counter 1211 receives a plurality of specimens. The specimen is a specimen for infectious disease testing. The infectious disease testing uses a PCR method.

The specimen collection robot module 1212 includes a plurality of (four) first robots 1212a. Each of the plurality of first robots 1004a performs a process using two robot arms. Each robot arm includes a horizontal joint and an elevating mechanism connected to the horizontal joint. The first robot 1212a holds a specimen collection container 1007a containing the specimen collected from the subject P, and disinfects the specimen collection container 1007a. The first robot 1212a supplies a dilute solution into the specimen collection container 1007a to dilute the specimen. The first robot 1212a places the specimen collection container 1007a containing the diluted specimen on a conveyance section 1221. The specimen collection robot module 1212 may include one, two, three, or five or more first robots 1212a.

The centrifugal robot module 1213 includes a plurality of (two) robots 1213a. Each of the plurality of first robots 1004b includes a vertical articulated robot arm. The robot 1213a puts the specimen collection container 1007a transported by the conveyance section 1221 into an agitator. The robot 1213a puts the agitated specimen collection container into a centrifuge. The centrifugal robot module 1213 may include one or three or more robots 1213a.

In a booth in which the centrifugal robot module 1213 is installed, a predetermined number of (four or more) specimen collection containers 1007a transported by the conveyance section 1221 are stored. The robot 1213a puts the predetermined number of stored specimen containers into the centrifuge according to the priority of processing. The robot 1213a places the centrifuged specimen collection container on a conveyance section 1222.

The opening-dispensing robot module 1214 includes a second robot 1214a and a third robot 1214b. The second robot 1214a includes two robot arms with horizontal joints. The third robot 1214b includes a vertical articulated robot arm. The second robot 1214a opens the specimen collection container 1007a transported by the conveyance section 1222. After opening the specimen collection container 1007a, the second robot 1214a dispenses the specimen in the specimen collection container 1007a onto a plate 1007b (96-well deep well plate). The second robot 1214a dispenses a plurality of reagents onto the plate 1007b (96-well deep well plate). The third robot 1214b places the plate 1007b (96-well deep well plate) onto which the specimen and the reagent have been dispensed on a conveyance section 1223.

The nucleic acid extraction robot module 1215 includes a plurality of (five) robots 1215a. The robot 1215a includes a vertical articulated robot arm. The robot 1215a moves the plate 1007b (96-well deep well plate) transported by the conveyance section 1223 to a workbench. The robot 1215a performs a nucleic acid extraction operation on the plate 1007b (96-well deep well plate) on the workbench. The robot 1215a dispenses the extracted nucleic acid into a multiple-connected tube 1007c (8-connected PCR tube). The robot 1215a places the multiple-connected tube 1007c (8-connected PCR tube) into which the nucleic acid extracted from the specimen has been dispensed on a conveyance section 1224. The nucleic acid extraction robot module 1215 may include one, two, three, four, or six or more robots 1215a.

The measurement robot module 1216 includes a robot 1216a and a fourth robot 1216b. The robot 1216a includes a vertical articulated robot arm. The fourth robot 1216b includes a vertical articulated robot arm. The robot 1216a prepares two types of reagents. The robot 1216a moves the multiple-connected tube 1007c (8-connected PCR tube) transported by the conveyance section 1224 to a workbench. The robot 1216a dispenses the prepared reagents into the multiple-connected tube 1007c (8-connected PCR tube) on the workbench, and performs suction and agitation. The fourth robot 1216b closes lids of the multiple-connected tube 1007c (8-connected PCR tube), and then puts the multiple-connected tube 1007c into a centrifuge. The fourth robot 1216b sets the multiple-connected tube 1007c (8-connected PCR tube) containing the centrifuged specimen in a thermal cycler. The fourth robot 1216b sets the heated multiple-connected tube 1007c (8-connected PCR tube) in a PCR testing device.

After determining a priority test specimen to be tested from among a plurality of specimens, the control device 1217 performs a control to start a process in order from the test specimen. Specifically, the control device 1217 includes a CPU (central processing unit) and a storage including a ROM (read-only memory) and a RAM (random access memory). The storage stores a PCR system management program. The control device 1217 manages and controls the airport PCR system 1210 based on the PCR system management program.

The main testing system 1220 determines whether the subject P is positive or negative based on the test result of the PCR testing device. The main testing system 1220 issues a document containing information on the test result of the PCR testing device. Specifically, the main testing system 1220 includes a controller 1220a including a CPU and a storage including a ROM and a RAM. The storage stores a test result determination program. The controller 1220*a* controls the main testing system 1220 based on the test result determination program.

Third Embodiment

A testing system 1300 according to a third embodiment is now described with reference to FIGS. 14 to 24. In this third embodiment, unlike the first embodiment, a structure in which a cabinet 1021 is not provided in an opening-dispensing unit 1500 of a second unit 1002*a* is described. As described below, in the opening-dispensing unit 1500 of the second unit 1002*a* according to the third embodiment, a plurality of robots perform a process, and thus the cabinet 1021 is not provided as a countermeasure against infection to a human body. Furthermore, the cabinet 1021 is not provided such that it is possible to expand the range of choices of the robots to be installed. For example, it is possible to select a smaller robot, or select a robot capable of high-speed operation to improve tact time.

Figure 14:
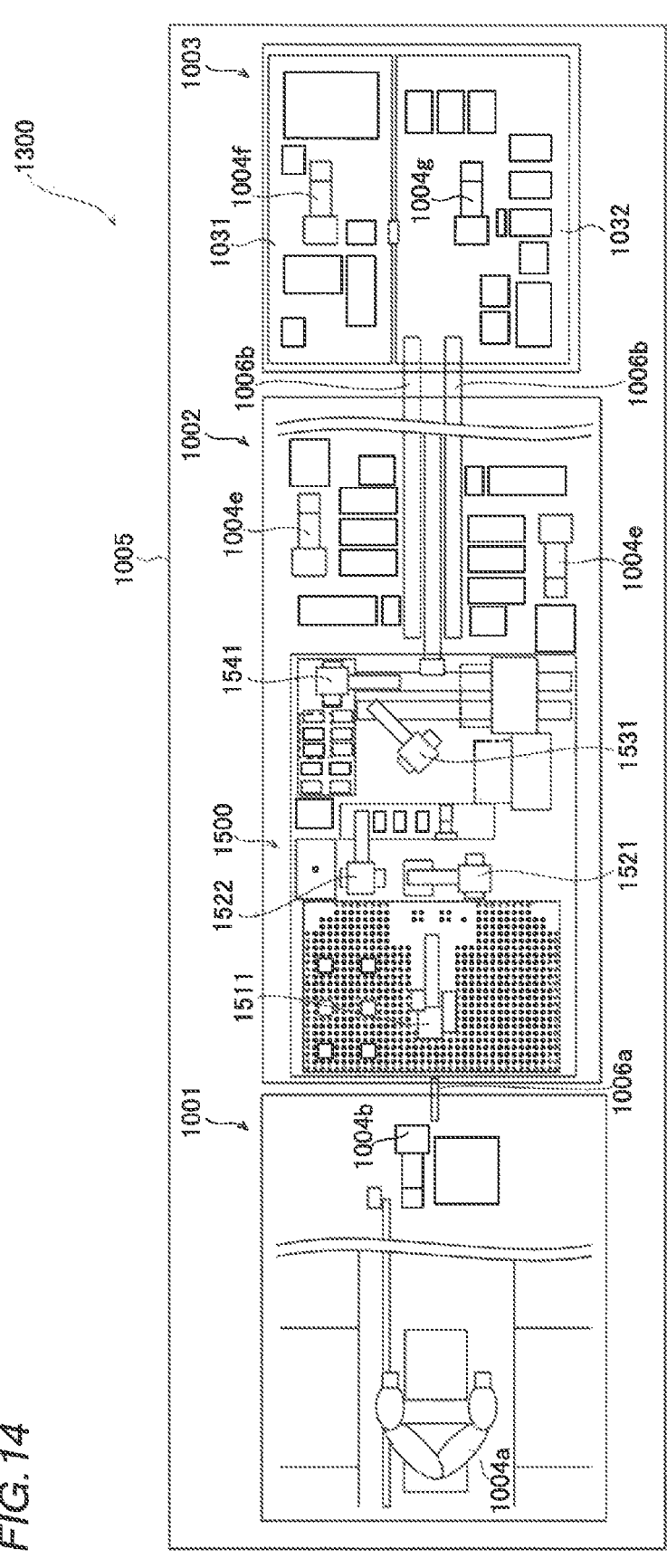
FIG. 14 is a diagram schematically showing the overall structure of a testing system according to a third embodiment.

As shown in FIG. 14, the testing system 1300 includes a first unit 1001, the second unit 1002*a*, and a third unit 1003. The second unit 1002*a* includes the opening-dispensing unit 1500. Robots 1004*a* and 1004*b* are provided in the first unit 1001 of the testing system 1300. Robots 1511, 1521, 1522, 1531, and 1004*e* are provided in the second unit 1002*a* of the testing system 1100. Robots 1004*f* and 1004*g* are provided in the third unit 1003 of the testing system 1300. The first unit 1001, the second unit 1002*a*, and the third unit 1003 are provided inside a container 1005. At least one of the first unit 1001, the second unit 1002*a*, or the third unit 1003 needs to be provided inside the container 1005. Thus, the testing system 1300 can be easily transported and installed.

The testing system 1300 also includes conveyance sections 1006*a* and 1006*b* that connect the first unit 1001, the second unit 1002*a*, and the third unit 1003 to each other. Specifically, the first unit 1001 and the second unit 1002*a* are connected to each other by the conveyance section 1006*a*. The second unit 1002*a* and the third unit 1003 are connected to each other by the conveyance sections 1006*b*. Thus, a specimen can be easily moved between the first unit 1001, the second unit 1002*a*, and the third unit 1003 by the conveyance sections 1006*a* and 1006*b*.

The first unit 1001 collects and receives the specimen. For example, in the first unit 1001, the specimen is collected from a subject, and the collected specimen is diluted with a dilute solution. In the first unit 1001, the diluted specimen is agitated. In the first unit 1001, the diluted specimen is centrifuged. The second unit 1002*a* is connected to the first unit 1001 and preprocesses the specimen before measurement. For example, in the second unit 1002*a*, a specimen dispensing process is performed as preprocessing of the specimen in the opening-dispensing unit 1500. Furthermore, in the second unit 1002*a*, a reagent dispensing process is performed as preprocessing of the specimen in the opening-dispensing unit 1500. Moreover, in the second unit 1002*a*, a nucleic acid extraction process is performed as preprocessing of the specimen downstream of the opening-dispensing unit 1500. The third unit 1003 is connected to the second unit 1002*a* and measures the preprocessed specimen. For example, in the third unit 1003, a process is performed to measure whether or not the specimen contains an infectious virus by an RT-PCR test.

Structure of Opening-Dispensing Unit

Figure 15:
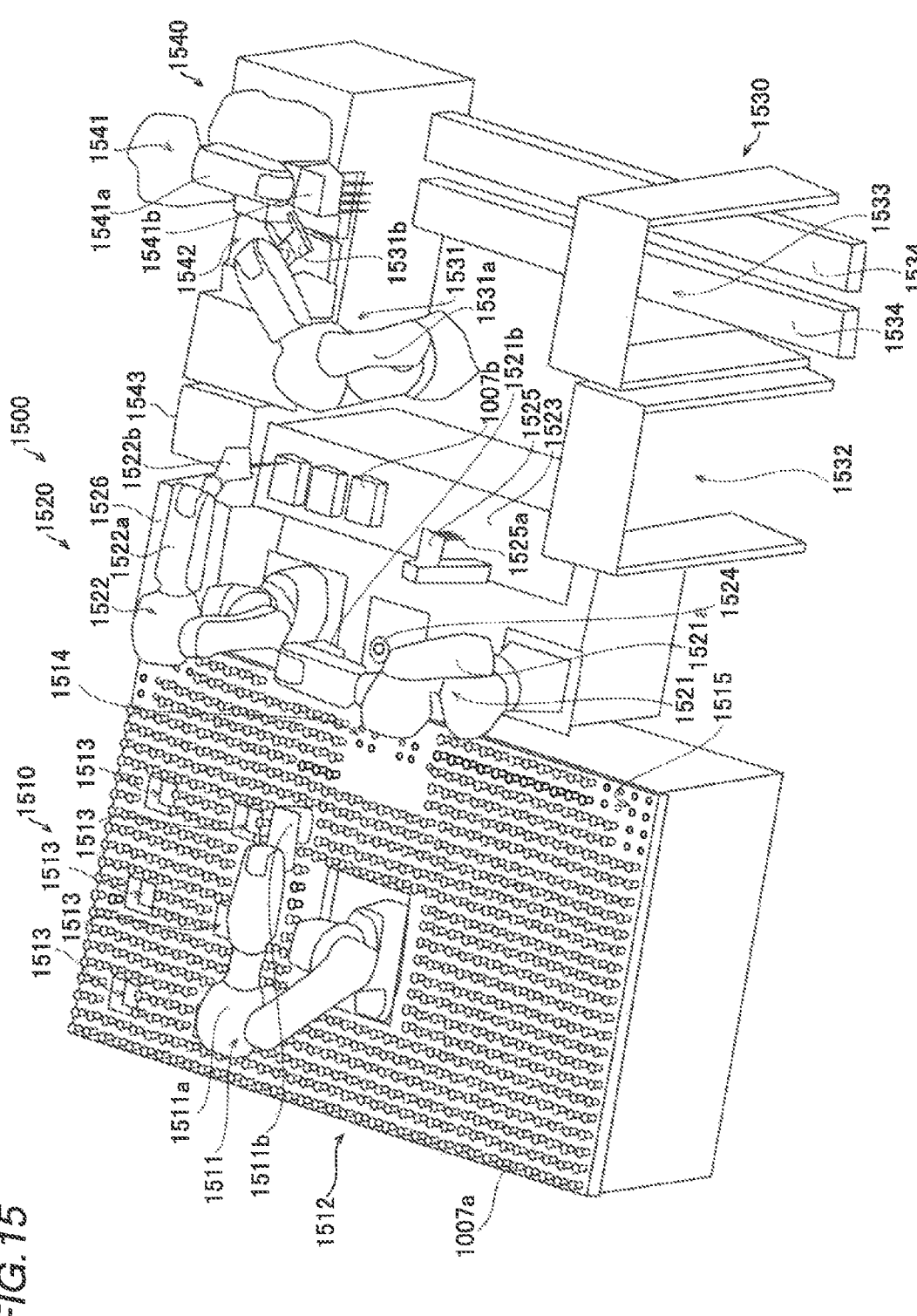
FIG. 15 is a perspective view showing a structure for performing an opening-dispensing process in a second unit of the testing system according to the third embodiment.
Figure 16:
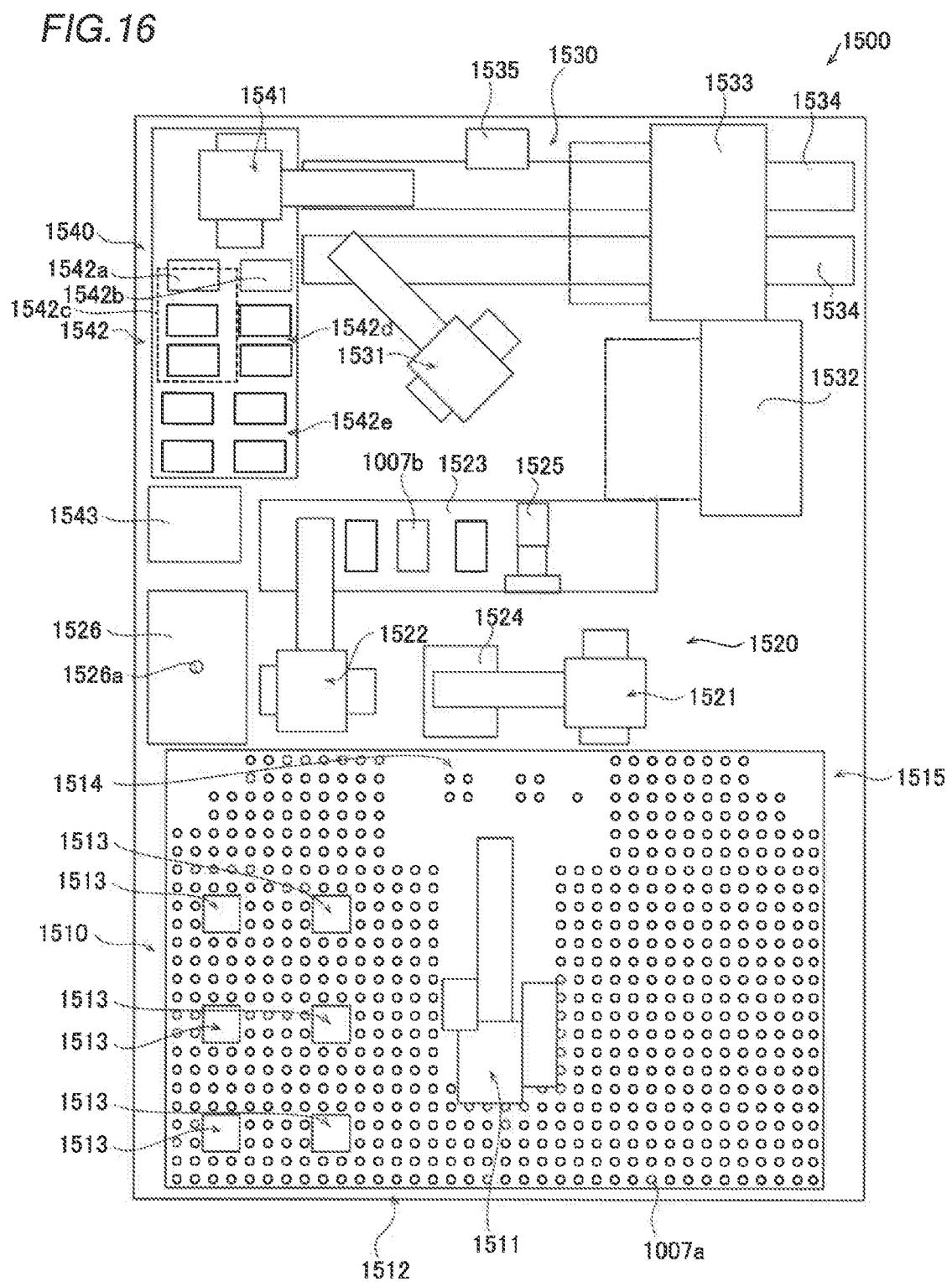
FIG. 16 is a plan view showing the structure for performing the opening-dispensing process in the second unit of the testing system according to the third embodiment.

As shown in FIGS. 15 and 16, a specimen storage 1510, a specimen dispenser 1520, a workpiece conveyance section 1530, and a reagent dispenser 1540 are provided in the opening-dispensing unit 1500. The opening-dispensing unit 1500 is maintained at a negative pressure lower than the air pressure of the outside of the opening-dispensing unit 1500 of the second unit 1002*a*.

Structure of Specimen Storage

The specimen storage 1510 stores a plurality of specimen collection containers 1007*a*. Specifically, the specimen storage 1510 stores, for a predetermined period of time, the specimen collection container 1007*a* containing the collected specimen, from which a portion of the specimen has been dispensed onto a plate 1007*b* and in which a remaining portion of the specimen has been contained. The specimen storage 1510 stores the specimen collection container 1007*a* for two hours, for example. Thus, when retesting is required, the specimen can be taken out from the specimen storage 1510 and retested, and thus there is no need to re-collect a specimen.

The specimen storage 1510 includes a moving robot 1511, a storage 1512, disposal sections 1513, a specimen placement section 1514, and a QC storage 1515. The specimen storage 1510 is provided between the specimen dispenser 1520 that dispenses the specimen and a centrifuge that performs centrifugal separation. The storage 1512 is an example of a first placement section. The specimen placement section 1514 is an example of a second placement section.

The moving robot 1511 moves the specimen collection container 1007*a* in the storage 1512. The moving robot 1511 receives the specimen collection container 1007*a* from the first unit 1001 (see FIG. 14) and places it on the specimen placement section 1514. The moving robot 1511 moves the specimen collection container 1007*a* from which the specimen has been dispensed from the specimen placement section 1514 to the storage 1512. The moving robot 1511 discards the specimen collection containers 1007*a* that have been stored for a predetermined period of time in the disposal sections 1513.

Figure 17:
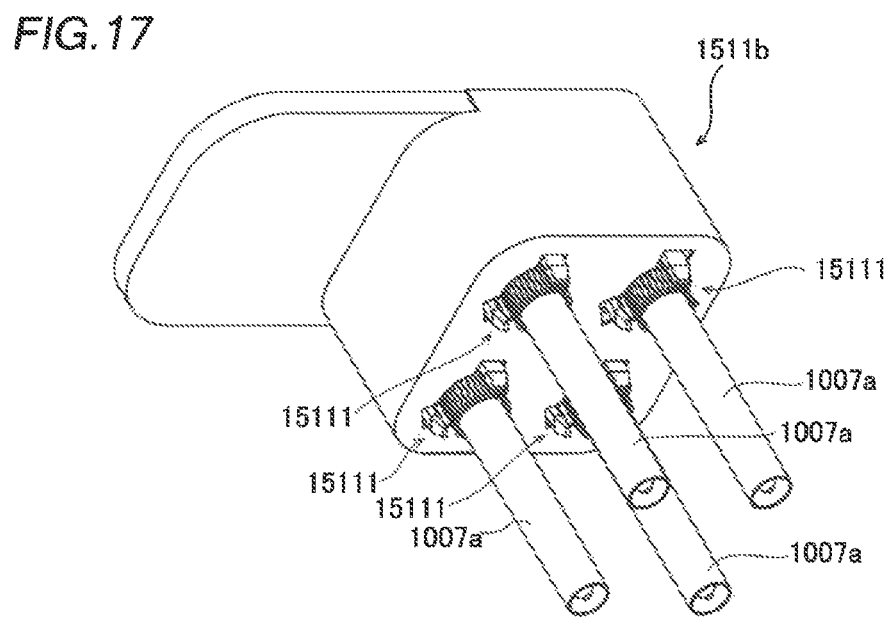
FIG. 17 is a diagram showing a hand of a moving robot of a specimen storage of the second unit of the testing system according to the third embodiment.

As shown in FIG. 15, the moving robot 1511 includes a robot body 1511*a* and a hand 1511*b* attached to the tip end of the robot body 1511*a*. The robot body 1511*a* is a vertically articulated robot including a plurality of vertical joints. The hand 1511*b* can grasp a plurality of (four) specimen collection containers 1007*a*, as shown in FIG. 17. The hand 1511*b* includes a plurality of (four) sets of chucks 15111. Each chuck 15111 has three claws and grasps the specimen collection container 1007*a* by opening and closing the three claws. Of the four sets of chucks 15111, three sets of chucks 15111 are driven by a common pneumatic source. Of the four sets of chucks 15111, the remaining one set of chucks 15111 is independently driven by a pneumatic source different from that for the other three sets of chucks 15111. Thus, it is possible to individually grasp the specimen collection container 1007*a* that needs to be grasped individually, such as the specimen collection container 1007*a* containing an interrupt specimen that is subjected to preprocessing and is to be measured with priority over other specimens.

As shown in FIGS. 15 and 16, a plurality of specimen collection containers 1007*a* can be placed in the storage 1512. The storage 1512 can store the number of (e.g., several hundred) specimen collection containers 1007*a* that can be processed (preprocessed and measured) in two hours, for example. The storage 1512 includes a plurality of holding holes into which the specimen collection containers 1007*a* are inserted in an upright state.

A plurality of (six) disposal sections 1513 are provided in the storage 1512 in a plan view. The specimen collection containers 1007a that have been stored for the predetermined period of time are discarded in the disposal sections 1513. The disposal sections 1513 include storages that can store the specimen collection containers 1007a for a predetermined amount of time (e.g., eight hours) under the pedestal.

The specimen collection container 1007a sent from the first unit 1001 (see FIG. 14) is placed on the specimen placement section 1514. In other words, the specimen collection container 1007a is placed on the specimen placement section 1514 before the specimen is dispensed from the specimen collection container 1007a. The specimen collection container 1007a placed on the specimen placement section 1514 is delivered to the specimen dispenser 1520, and after the specimen is dispensed, the specimen collection container 1007a is returned to the specimen placement section 1514 again. After the specimen has been dispensed, the specimen collection container 1007a that has been returned to the specimen placement section 1514 is moved to the storage 1512. The specimen collection container 1007a that needs to be checked by an operator due to an unreadable identifier of the specimen collection container 1007a, for example, is ejected from the specimen placement section 1514 to the outside by a chute.

The QC storage 1515 stores positive control and negative control reagents for quality control. The positive control and negative control reagents stored in the QC storage 1515 are dispensed for each predetermined number of specimens (e.g., every several tens) and sent for measurement.

The specimen dispenser 1520 dispenses the specimen from the specimen collection container 1007a onto the plate 1007b. Specifically, the specimen dispenser 1520 opens the specimen collection container 1007a, dispenses a portion of the specimen from the opened specimen collection container 1007a onto the plate 1007b, and closes the specimen collection container 1007a after the dispensing.

Structure of Specimen Dispenser

The specimen dispenser 1520 includes an opening robot 1521, a dispensing robot 1522, a workbench 1523, an opening gripper 1524, a dissolution/adsorption liquid dispensing device 1525, and a disposal section 1526.

Figure 18:
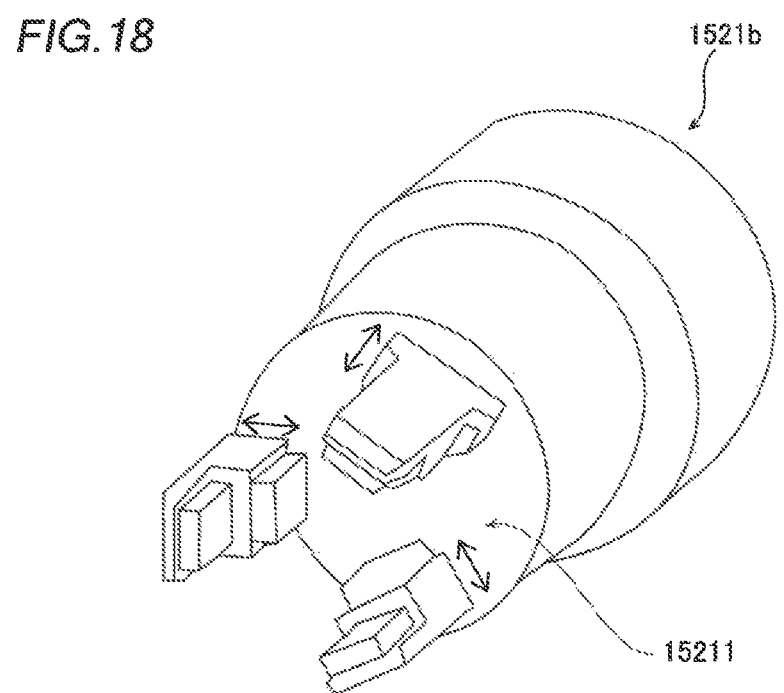
FIG. 18 is a diagram showing a hand of an opening robot of a specimen dispenser of the second unit of the testing system according to the third embodiment.

As shown in FIG. 15, the opening robot 1521 includes a robot body 1521a and a hand 1521b attached to the tip end of the robot body 1521a. The robot body 1521a is a vertically articulated robot including a plurality of vertical joints. The hand 1521b includes a chuck 15211, as shown in FIG. 18. The chuck 15211 has three claws and grasps a lid 1071 of the specimen collection container 1007a by opening and closing the three claws.

Figure 19:
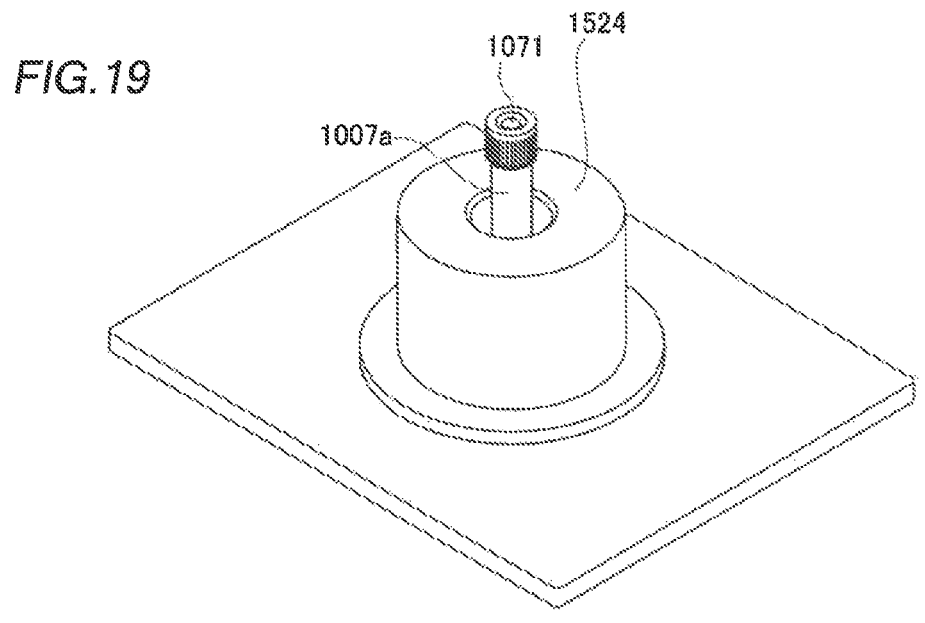
FIG. 19 is a diagram showing an opening gripper of the specimen dispenser of the second unit of the testing system according to the third embodiment.

As shown in FIG. 19, the opening gripper 1524 grasps the placed specimen collection container 1007a such that the placed specimen collection container 1007a is not rotated. The opening gripper 1524 includes a reader to read the identifier of the specimen collection container 1007a. Furthermore, the opening gripper 1524 includes a detection sensor to detect the open and closed states of the lid 1071. The detection sensor includes a camera-equipped laser sensor, for example.

The opening robot 1521 opens the specimen collection container 1007a from which the specimen is dispensed. Specifically, the opening robot 1521 receives the specimen collection container 1007a placed on the specimen placement section 1514 of the specimen storage 1510 and moves it to the opening gripper 1524. Then, the opening robot 1521 grasps the lid 1071 (see FIG. 4) of the specimen collection container 1007a grasped by the opening gripper 1524 and rotates it in an open direction to open the specimen collection container 1007a. As shown in FIG. 19, the opening robot 1521 grasps the lid 1071 of the specimen collection container 1007a with the chuck 15211 and rotates it in a closing direction to close the specimen collection container 1007a while the specimen collection container 1007a from which the specimen has been dispensed is grasped by the opening gripper 1524. Then, the opening robot 1521 moves the closed specimen collection container 1007a to the specimen placement section 1514 of the specimen storage 1510. The opening robot 1521 receives, opens, and closes positive control and negative control containers for quality control similarly to the specimen collection container 1007a.

As shown in FIGS. 15 and 16, the dispensing robot 1522 dispenses the specimen from the specimen collection container 1007a onto the plate 1007b. Specifically, the dispensing robot 1522 suctions the specimen from the opened specimen collection container 1007a and discharges the suctioned specimen to a predetermined position on the plate 1007b. The dispensing robot 1522 dispenses the reagents from the positive control and negative control containers for quality control onto the plate 1007b similarly to the specimen collection container 1007a.

Figure 20:
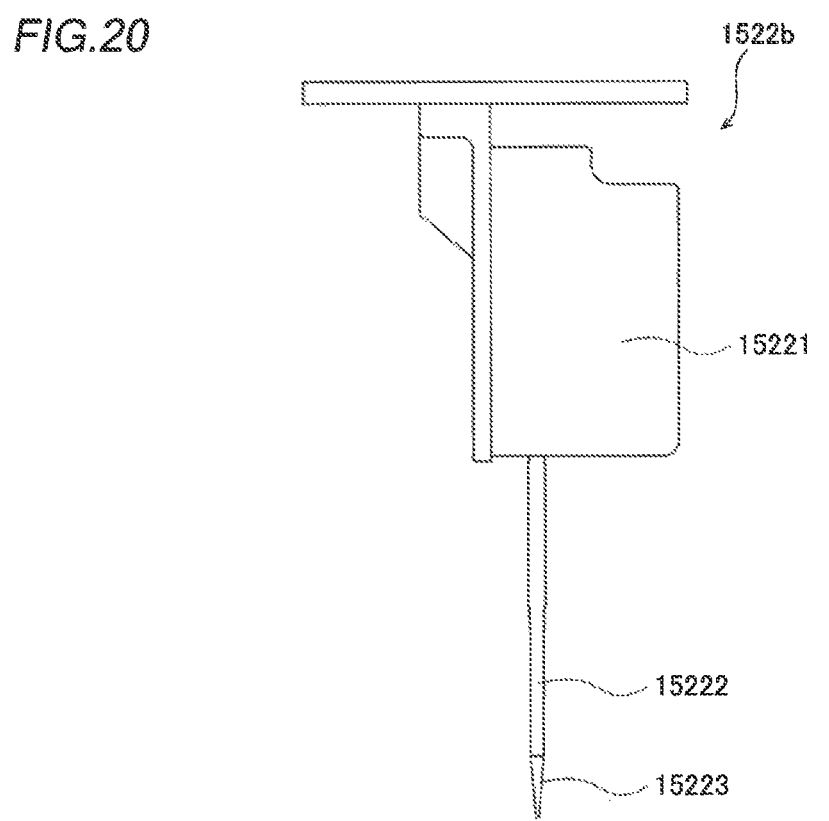
FIG. 20 is a diagram showing a hand of a dispensing robot of the specimen dispenser of the second unit of the testing system according to the third embodiment.

As shown in FIG. 15, the dispensing robot 1522 includes a robot body 1522a and a hand 1522b attached to the tip end of the robot body 1522a. The robot body 1522a is a vertically articulated robot including a plurality of vertical joints. The hand 1522b includes a body 15221 and a nozzle 15222, as shown in FIG. 20. A disposable tip 15223 is detachably attached to the tip end of the nozzle 15222. The body 15221 supplies a negative pressure and a positive pressure to the nozzle 15222 to suction and discharge the specimen. Furthermore, the body 15221 detects the liquid level in the container by detecting the pressure in the nozzle 15222. Then, based on the detection result of the liquid level and the tip end position of the tip 15223 lowered by the dispensing robot 1522, the water level (the amount of specimen or the amount of reagent) in the container is acquired. The dispensing robot 1522 takes a new tip 15223 from the workbench 1523 each time it dispenses the specimen, and discards the used tip 15223 in the disposal section 1526 after dispensing the specimen.

As shown in FIGS. 15 and 16, on the workbench 1523, the plate 1007b onto which the reagents and the specimen are dispensed is placed. Furthermore, on the workbench 1523, a tip rack that accommodates a plurality of tips 15223 attached to the tip end of the hand 1522b of the dispensing robot 1522 is placed.

As shown in FIG. 15, the dissolution/adsorption liquid dispensing device 1525 dispenses a dissolution/adsorption liquid onto the plate 1007b. Specifically, the dissolution/adsorption liquid dispensing device 1525 is provided on the workbench 1523. The dissolution/adsorption liquid dispensing device 1525 dispenses the dissolution/adsorption liquid onto the plate 1007b grasped by a transfer robot 1531 of the workpiece conveyance section 1530. The dissolution/adsorption liquid dispensing device 1525 includes a plurality of (four) nozzles 1525a, and can concurrently dispense the dissolution/adsorption liquid to four wells 1073 (see FIG. 9) of the plate 1007b. The dissolution/adsorption liquid dispensing device 1525 moves the plate 1007b by the transfer robot 1531 and dispenses the dissolution/adsorption liquid into eight wells 1073 for one plate 1007b by two operations. The dissolution/adsorption liquid dispensing device 1525 includes a flow rate sensor for each of the four nozzles 1525a, and dispenses the dissolution/adsorption liquid with a dispense pump that performs dispensing by switching between four ports.

In the disposal section 1526, the used tip 15223 used for specimen dispensing is discarded. The disposal section 1526 has a small disposal port 1526a on the upper surface, and the tip 15223 is put through the disposal port 1526a. In the disposal section 1526, a medical pail (a container with a lid that stores potentially infectious waste) that stores the tip 15223 is arranged below the disposal port 1526a.

Structure of Workpiece Conveyance Section

The workpiece conveyance section 1530 transports a workpiece within the opening-dispensing unit 1500. Specifically, the workpiece conveyance section 1530 transports the plate 1007b onto which the specimen is dispensed. Furthermore, the workpiece conveyance section 1530 transports the tip rack containing the tips 15223 (see FIG. 20) used in the specimen dispenser 1520. The workpiece conveyance section 1530 transports a tip rack containing tips 15413 (see FIG. 22) used in the reagent dispenser 1540.

As shown in FIGS. 15 and 16, the workpiece conveyance section 1530 includes the transfer robot 1531, a shelf 1532, a shelf 1533, a plurality of (two) plate conveyance sections 1534, and a plate deliverer 1535.

The transport robot 1531 grasps and transports the plate 1007b. Specifically, the transport robot 1531 receives the plate 1007b from the plate conveyance sections 1534 and transports it to the workbench 1523. The transport robot 1531 grasps and moves the plate 1007b when the dissolution/adsorption liquid is dispensed by the dissolution/adsorption liquid dispensing device 1525. The transport robot 1531 transports the plate 1007b onto which the dissolution/adsorption liquid has been dispensed to a position on the workbench 1523 at which the specimen is dispensed. The transport robot 1531 transports the plate 1007b onto which the specimen has been dispensed to a workbench 1542 of the reagent dispenser 1540. The transport robot 1531 transports the plate 1007b onto which reagents have been dispensed on the workbench 1542 to the plate deliverer 1535.

The transport robot 1531 takes out the tip rack containing the tips 15223 (see FIG. 20) used in the specimen dispenser 1520 from the shelf 1532 and transports it to the workbench 1523. The transport robot 1531 transports the tip rack containing the tips 15413 (see FIG. 22) used in the reagent dispenser 1540 to the workbench 1542 of the reagent dispenser 1540. The transport robot 1531 transports an inner lid of the tip rack to a lid disposal section 1543 and discards it.

Figure 21:
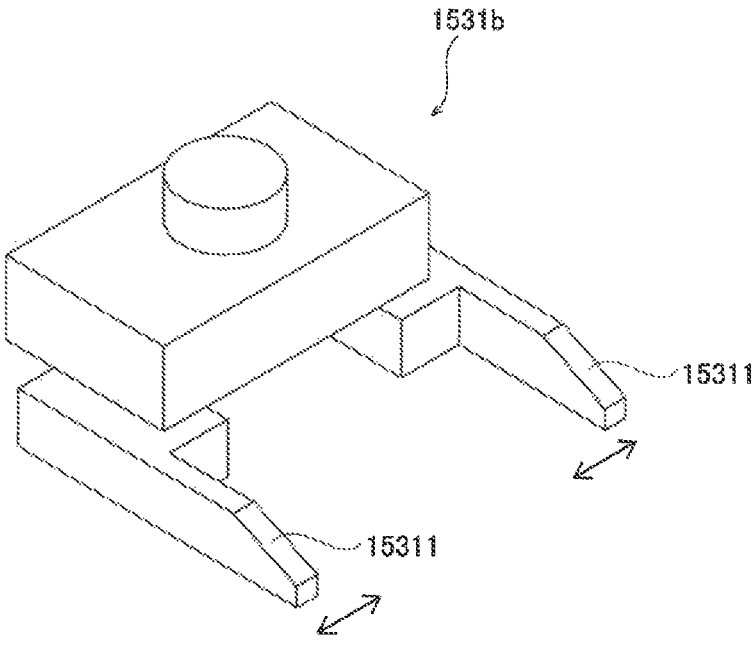
FIG. 21 is a diagram showing a hand of a transfer robot of a workpiece conveyance section of the second unit of the testing system according to the third embodiment.

The transport robot 1531 includes a robot body 1531a and a hand 1531b attached to the tip end of the robot body 1531a. The robot body 1531a is a vertically articulated robot including a plurality of vertical joints. The hand 1531b includes a pair of chuck claws 15311, as shown in FIG. 21. The pair of chuck claws 15311 grasp the plate 1007b or the tip rack by opening and closing.

As shown in FIGS. 15 and 16, the shelf 1532 stores the tip rack containing the tips 15223 (see FIG. 20) used in the specimen dispenser 1520. Furthermore, the shelf 1532 stores the reagents (magnetic particles, proK reagent) used in the reagent dispenser 1540. A drawer is provided on the shelf 1532, and the stored tip rack and reagents are taken out by the transfer robot 1531 with the drawer drawn out. The tip rack and the reagents can be supplied from the outside to the shelf 1532 by the operator.

The shelf 1533 stores the tip rack containing the tips 15413 (see FIG. 22) used in the reagent dispenser 1540. A drawer is provided on the shelf 1533, and the stored tip rack is taken out by the transfer robot 1531 with the drawer drawn out. The tip rack can be supplied from the outside to the shelf 1533 by the operator.

The plate conveyance sections 1534 transport a new plate 1007b before use. The two plate conveyance sections 1534 are provided parallel to each other. The two plate conveyance sections 1534 each include a conveyor to transport the plate 1007b.

The plate deliverer 1535 is provided to deliver the plate 1007b onto which the specimen and the reagents have been dispensed to a downstream unit that performs the nucleic acid extraction process.

Structure of Reagent Dispenser

The reagent dispenser 1540 dispenses the reagents onto the plate 1007b. Specifically, the reagent dispenser 1540 dispenses the magnetic particles and the proK reagent onto the plate 1007b onto which the specimen has been dispensed.

The reagent dispenser 1540 includes a dispensing robot 1541, the workbench 1542, and the lid disposal section 1543.

The dispensing robot 1541 dispenses the magnetic particles accommodated in the plate 1007b placed on an agitator 1542a of the workbench 1542 onto the plate 1007b onto which the specimen has been dispensed. Specifically, the dispensing robot 1541 suctions the magnetic particles agitated by the agitator 1542a and discharges the suctioned magnetic particles to a predetermined position on the plate 1007b. The dispensing robot 1541 dispenses the proK reagent accommodated in the plate 1007b placed on a cooler 1542b of the workbench 1542 onto the plate 1007b onto which the specimen has been dispensed. Specifically, the dispensing robot 1541 suctions the proK reagent cooled by the cooler 1542b and discharges the suctioned proK reagent to a predetermined position on the plate 1007b.

Figure 22:
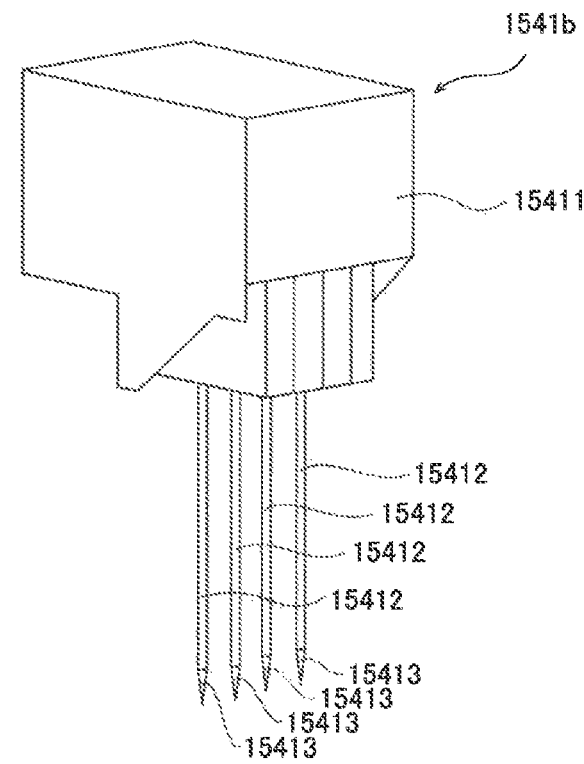
FIG. 22 is a diagram showing a hand of a dispensing robot of a reagent dispenser of the second unit of the testing system according to the third embodiment.

The dispensing robot 1541 includes a robot body 1541a and a hand 1541b attached to the tip end of the robot body 1541a. The robot body 1541a is a vertically articulated robot including a plurality of vertical joints. The hand 1541b includes a body 15411 and a plurality of (four) nozzles 15412, as shown in FIG. 22. The disposable tip 15413 is detachably attached to the tip end of each of the plurality of nozzles 15412. The body 15411 supplies a negative pressure and a positive pressure to the plurality of nozzles 15412 to suction and discharge the specimen. The dispensing robot 1541 dispenses both the magnetic particles and the proK reagent into each of the eight wells 1073 into which the specimen has been dispensed for one plate 1007b. That is, the dispensing robot 1541 dispenses one of the magnetic particles and the proK reagent into the four wells 1073 using the four nozzles 15412, and then dispenses one of the magnetic particles and the proK reagent into the remaining four wells 1073 using the four nozzles 15412. Then, the dispensing robot 1541 replaces the used tips 15413 with new tips 15413. Then, the dispensing robot 1541 dispenses the other of the magnetic particles and the proK reagent into the four wells 1073 using the four nozzles 15412, and then dispenses the other of the magnetic particles and the proK reagent into the remaining four wells 1073 using the four nozzles 15412. In other words, the dispensing robot 1541 dispenses the magnetic particles and the proK reagent by performing a total of four dispensing operations with respect to the eight wells 1073 of one plate 1007b.

As shown in FIG. 16, on the workbench 1542, the agitator 1542a, the cooler 1542b, a disposal section 1542c, a plate placement section 1542d, and a waiting section 1542e are provided.

The plate 1007b containing the magnetic particles is placed on the agitator 1542a, and the agitator 1542a vibrates the plate 1007b so as to diffuse the magnetic particles.

The plate 1007*b* containing the proK reagent is placed on the cooler 1542*b*, and the cooler 1542*b* cools the proK reagent to about 4° C.

The disposal section 1542*c* is provided below the workbench 1542, and the tips 15413 used for reagent dispensing by the dispensing robot 1541 are discarded.

The plate 1007*b* onto which the specimen has been dispensed is placed on the plate placement section 1542*d*, and the reagents (the magnetic particles and the proK reagent) are dispensed onto the placed plate 1007*b* by the dispensing robot 1541.

The plate 1007*b* onto which the specimen has been dispensed is placed on the waiting section 1542*e* to wait for inactivation.

The inner lid of the tip rack is discarded in the lid disposal section 1543.

Structure of Third Unit

Figure 23:
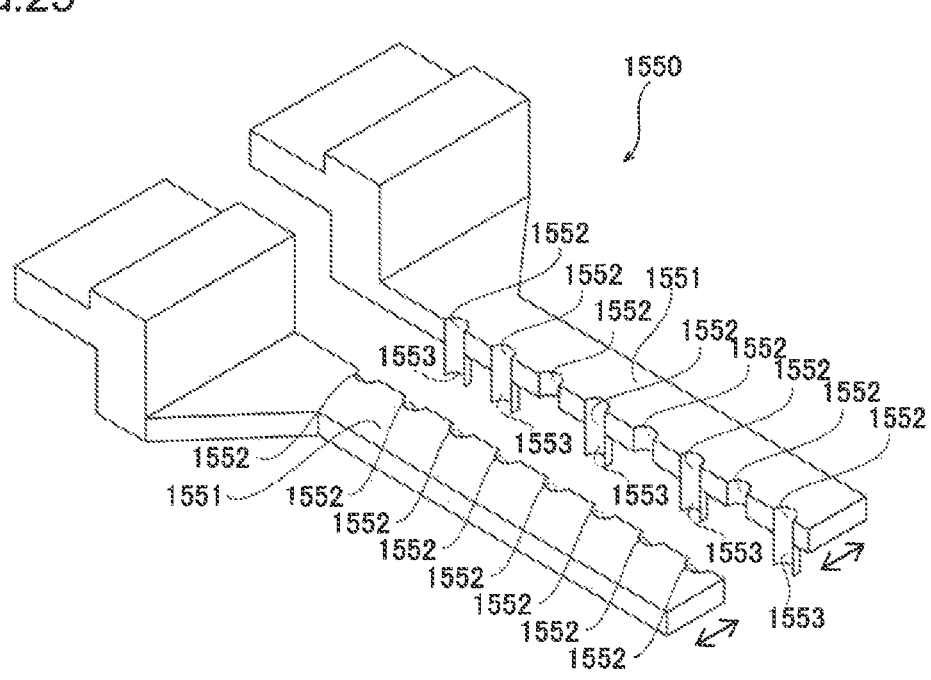
FIG. 23 is a perspective view showing a hand for grasping a multiple-connected tube in a third unit of the testing system according to the third embodiment.

As shown in FIG. 14, the third unit 1003 includes a reagent preparation room 1031 to prepare a reagent for measuring the specimen, and a measurement room 1032 to measure the specimen. The third unit 1003 includes the fourth robot 1004*g* to transport a multiple-connected tube 1007*c*. As shown in FIG. 23, the fourth robot 1004*g* includes a hand 1550 to grasp the multiple-connected tube 1007*c*.

The hand 1550 includes a pair of chuck claws 1551. Each of the pair of chuck claws 1551 includes a plurality of (eight) grasping portions 1552 to sandwich and grasp a plurality of (eight) tubes 1074 of the multiple-connected tube 1007*c*. Five of the eight grasping portions 1552 include contact portions 1553. The contact portions 1553 reduce or prevent falling of the tubes 1074 when lids 1075 of the tubes 1074 are closed.

The plurality of grasping portions 1552 are each formed in a concave shape in a plan view. The grasping portions 1552 are subjected to anti-slip finishing. For example, the grasping portions 1552 are diamond knurled or baked with butyl rubber.

Figure 24:
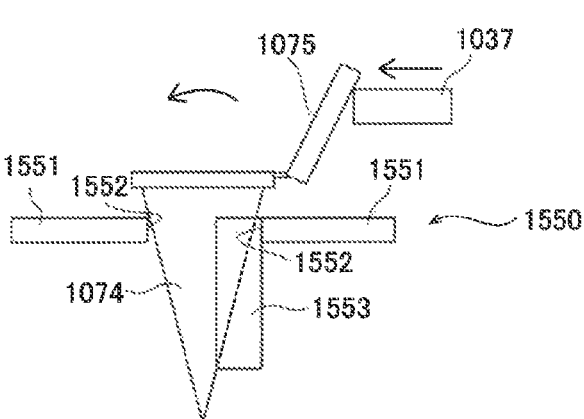
FIG. 24 is a side view showing the hand for grasping the multiple-connected tube in the third unit of the testing system according to the third embodiment.

As shown in FIG. 24, the contact portions 1553 are provided at least below the grasping portions 1552 on the side on which a lid closer 1037 contacts the lids 1075. The contact portions 1553 contact the tubes 1074 when the lids 1075 are pushed relatively by the lid closer 1037. Thus, it is possible to reduce or prevent falling of the tubes 1074, and thus the lids 1075 can be reliably closed.

Fourth Embodiment

A testing equipment system 1 according to a fourth embodiment is now described with reference to FIGS. 25 to 31.

Structure of Testing Equipment System

Figure 25:
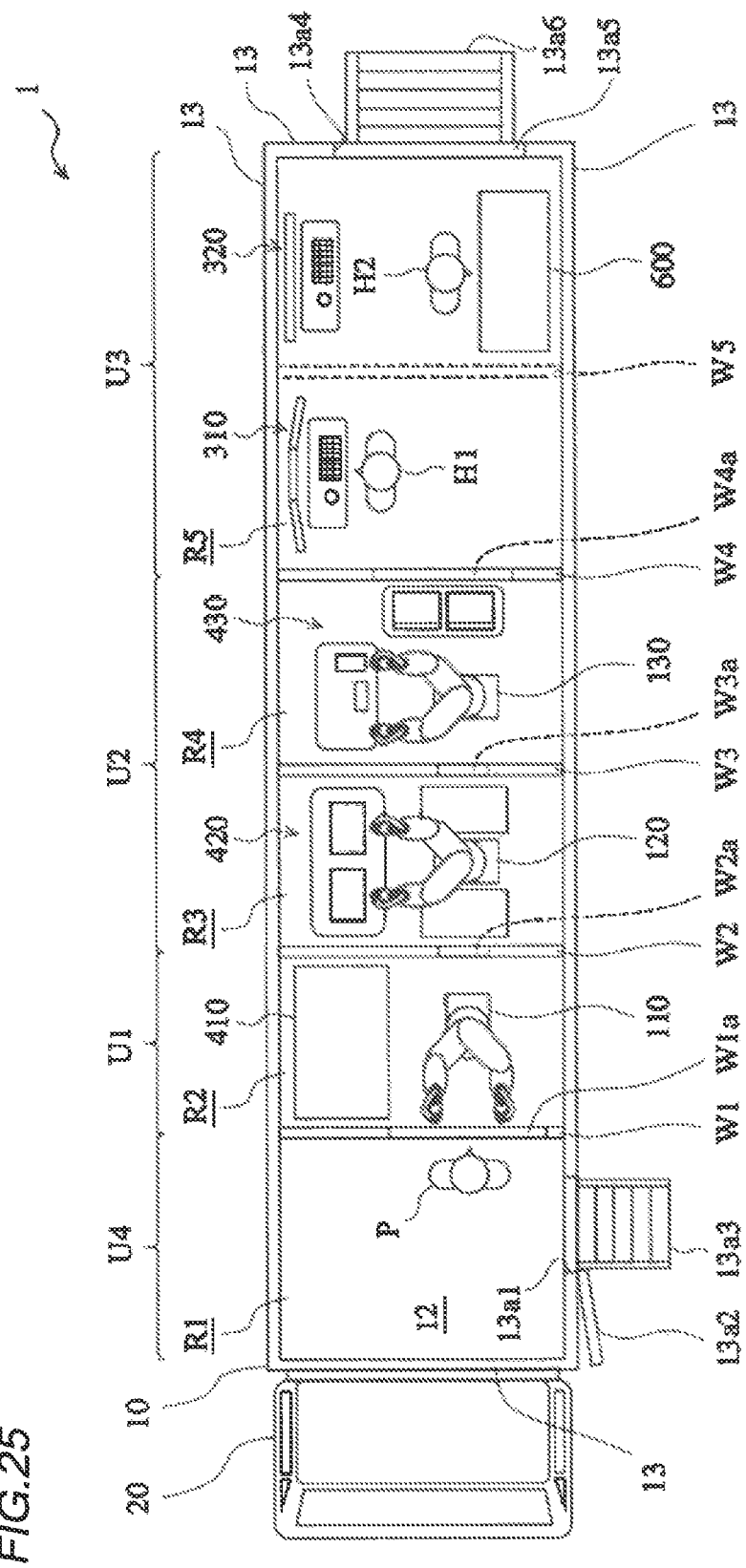
FIG. 25 is a plan view showing an example of the structure of a testing equipment system according to a fourth embodiment.
Figure 26:
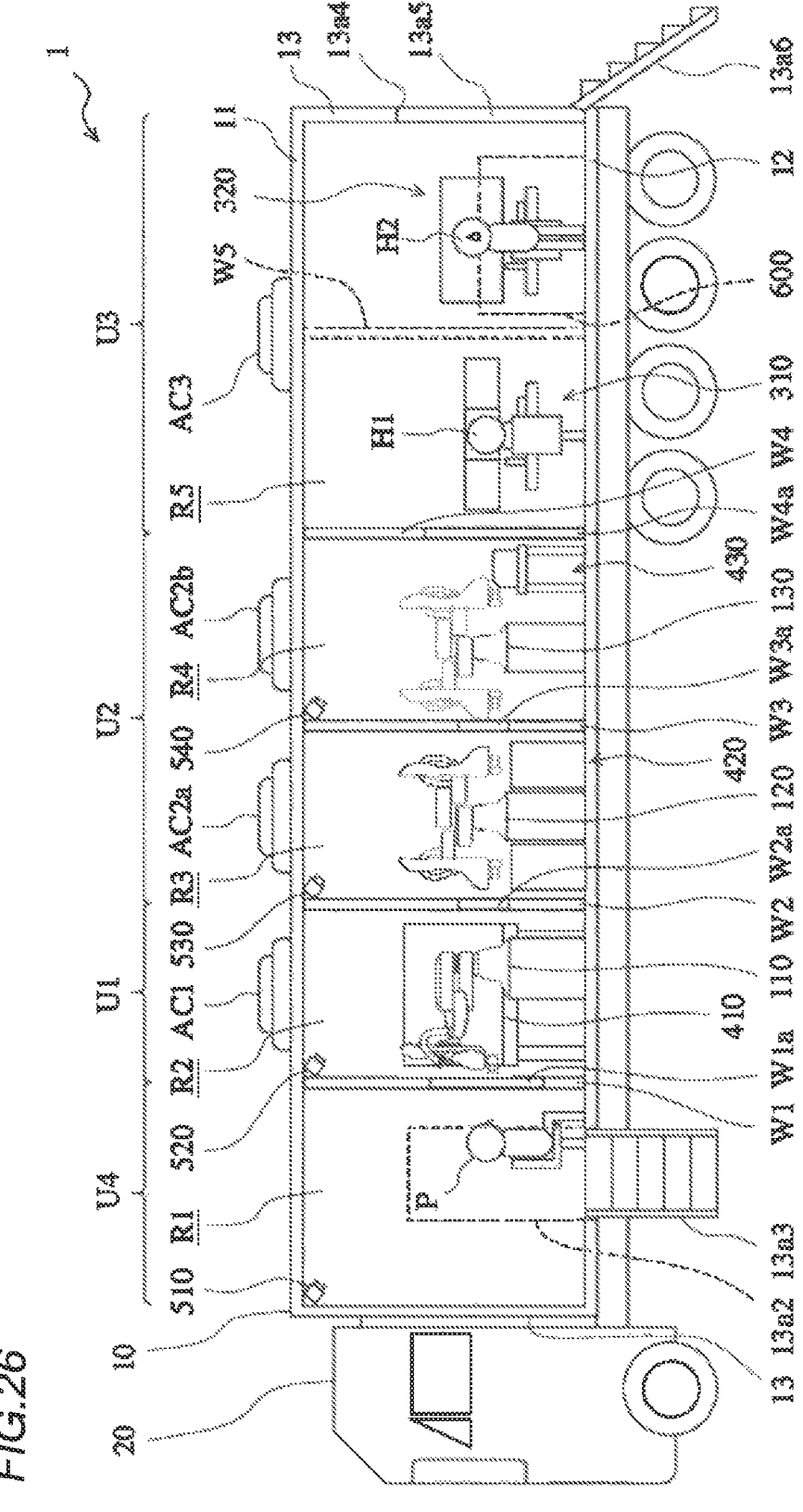
FIG. 26 is a sectional side view showing an example of the structure of the testing equipment system according to the fourth embodiment.

FIG. 25 is a plan view showing an example of the structure of the testing equipment system 1 according to the fourth embodiment. FIG. 26 is a sectional side view showing an example of the structure of the testing equipment system 1 according to the fourth embodiment. As shown in FIGS. 25 and 26, the testing equipment system 1 is a system for collecting a specimen from a subject P and measuring the specimen. In the following embodiment, the testing equipment system 1 is described as a system for collecting and measuring a specimen for PCR testing for analysis. The testing equipment system 1 includes a box 10 to house equipment for collecting and measuring the specimen for analysis, and a mobile body 20 on which the box 10 is loaded.

The box 10 isolates the interior space of the box 10 from the exterior space. The box 10 may be formed in advance into a box shape and be loaded on the mobile body 20 by a machine. Such a box 10 may be a container that may also be used for freight transport, for example. The box 10 may be loaded onto the mobile body 20 by a cargo-handling machine such as a forklift or a crane. The box 10 may be assembled on or within the mobile body 20. In the fourth embodiment, the box 10 is a container.

The mobile body 20 can move with the box 10 loaded thereon, and its specific structure is not particularly limited. The mobile body 20 may include a driving device or the like and be movable by itself, or may be moved by being towed or pushed by another mobile body. For example, the mobile body 20 may be a large motor vehicle such as a truck or a towed motor vehicle such as a trailer that can travel on the ground. The structure for moving the mobile body 20 on the ground is not limited to wheels, and may be crawlers or legs capable of walking, such as legs of a robot, for example. For example, the mobile body 20 may be a locomotive or a towed vehicle, such as a railroad train, capable of moving on a track. For example, the mobile body 20 may be a marine vessel that can navigate on the water surface or in the water by itself, or a barge that cannot navigate on the water surface or in the water by itself. For example, the mobile body 20 may be a fixed-wing aircraft such as an airplane or a rotary-wing aircraft such as a helicopter. In the fourth embodiment, the mobile body 20 is a large motor vehicle.

The testing equipment system 1 can be moved to various locations by the mobile body 20. Furthermore, the testing equipment system 1 can be placed at any location as long as the location has a space in which the mobile body 20 or the box 10 is accommodated.

The testing equipment system 1 is placed at a moving base for passenger transportation. The testing equipment system 1 can be moved to a starting point or an end point of movement across a geographical boundary and placed at that point, for example. The testing equipment system 1 may be used with the box 10 loaded on the mobile body 20, or may be used with the box 10 unloaded from the mobile body 20 to the ground or the like. In the fourth embodiment, the testing equipment system 1 is used with the box 10 loaded on the mobile body 20. The geographical boundary is not particularly limited, but may be a national border, a boundary of an administrative district such as a prefecture or a state, a boundary of an autonomous district, or a boundary between islands by sea, for example. The starting point or end point of movement across the geographical boundary may be an airport, a sea or river port, a railroad station, a bus station, a motorway entrance or exit, or a border crossing, for example.

The testing equipment system 1 includes a first unit portion U1 to a fourth unit portion U4 in the box 10. The box 10 houses the entirety of the first to fourth unit portions U1 to U4. The first unit portion U1 to the fourth unit portion U4 are integral and unitary with the box 10 to form one unit. That is, the testing equipment system 1 is made up of one unit.

The first unit portion U1 is a portion forming a collection room R2 including equipment for collecting the specimen from the subject P.

The second unit portion U2 is a portion forming analysis rooms R3 and R4 including equipment for measuring and analyzing the specimen, separately from the collection room R2. The second unit portion U2 reduces or prevents entry of pathogens present in the air into the analysis rooms R3 and R4 by floating, scattering, etc. The second unit portion U2 includes a first analysis unit portion that forms the first analysis room R3 and a second analysis unit portion that forms the second analysis room R4.

The third unit portion U3 is a unit portion including a result output device 600, which is an example of equipment to output an analysis result. Although not limited to this, in the fourth embodiment, the third unit portion U3 forms an accommodation room R5 that accommodates medical staffs H1 and H2, separately from the collection room R2, and includes the result output device 600 in the accommodation room R5. The third unit portion U3 reduces or prevents entry of pathogens present in the air into the accommodation room R5. Although not limited to this, in the fourth embodiment, the medical staff H1 is a doctor, and the medical staff H2 is a laboratory technician. Hereinafter, the "medical staff H1" may be written as a "doctor H1", and the "medical staff H2" may be written as a "laboratory technician H2".

The fourth unit portion U4 is a portion forming an examination room R1 to examine the subject P to collect the specimen from the subject P, separately from the analysis rooms R3 and R4. The fourth unit portion U4 reduces or prevents entry of pathogens present in the air into the analysis rooms R3 and R4.

The examination room R1 is adjacent to the collection room R2. The examination room R1 is surrounded by a top wall 11, a bottom wall 12, and three adjacent side walls 13 of the box 10, and separated from the collection room R2 by a partition wall W1. The partition wall W1 is fixed to the box 10 and is immovable. An opening is formed in the partition wall W1, and a transparent partition plate W1a made of glass or the like is fitted into the opening. The partition plate W1a has an opening that enables access between the examination room R1 and the collection room R2 to collect the specimen from the subject P.

An access opening 13a1 is formed in the side wall 13, which is one of the side walls 13 surrounding the examination room R1 and is adjacent to the partition wall W1, to allow the subject P to enter and exit the examination room R1, and a door 13a2 is arranged in the access opening 13a1 to open and close the access opening 13a1. The door 13a2 may be opened and closed by power such as electricity, or may be manually opened and closed. The door 13a2 has the ability to shield the access opening 13a1. Stairs 13a3 for ascending to and descending from the access opening 13a1 are stowably and deployably or detachably arranged in the access opening 13a1. The examination room R1 can be isolated from the outside of the box 10.

The collection room R2 is adjacent to the examination room R1 and the first analysis room R3. The examination room R1 and the first analysis room R3 are located on opposite sides of each other with the collection room R2 interposed therebetween. The collection room R2 is surrounded by the top wall 11, the bottom wall 12, and two opposing side walls 13 of the box 10, separated from the examination room R1 by the partition wall W1, and separated from the first analysis room R3 by a partition wall W2. The partition wall W2 is fixed to the box 10 and is immovable. An opening is formed in the partition wall W2, and a shutter W2a is arranged in the opening to open and close the opening. The shutter W2a is a sliding door that opens and closes the opening by being driven by an electric motor to be slid. The shutter W2a has the ability to shield the opening. The collection room R2 communicates with the examination room R1, but can be isolated from the first analysis room R3.

The first analysis room R3 is adjacent to the collection room R2 and the second analysis room R4. The collection room R2 and the second analysis room R4 are located on opposite sides of each other with the first analysis room R3 interposed therebetween. The first analysis room R3 is surrounded by the top wall 11, the bottom wall 12, and two opposing side walls 13 of the box 10, separated from the collection room R2 by the partition wall W2, and separated from the second analysis room R4 by a partition wall W3. The partition wall W3 is fixed to the box 10 and is immovable. An opening is formed in the partition wall W3, and a shutter W3a is arranged in the opening to open and close the opening. The shutter W3a is a sliding door that opens and closes the opening by being driven by an electric motor to be slid. The shutter W3a has the ability to shield the opening. The first analysis room R3 can be isolated from the collection room R2 and the second analysis room R4.

The second analysis room R4 is adjacent to the first analysis room R3 and the accommodation room R5. The first analysis room R3 and the accommodation room R5 are located on opposite sides of each other with the second analysis room R4 interposed therebetween. The second analysis room R4 is surrounded by the top wall 11, the bottom wall 12, and two opposing side walls 13 of the box 10, separated from the first analysis room R3 by the partition wall W3, and separated from the accommodation room R5 by a partition wall W4. The partition wall W4 is fixed to the box 10 and is immovable. An opening is formed in the partition wall W4, and a door W4a is arranged in the opening to open and close the opening. The door W4a may be opened and closed by power such as electricity, or may be manually opened and closed. The door W4a has the ability to shield the opening. The second analysis room R4 can be isolated from the first analysis room R3 and the accommodation room R5.

The accommodation room R5 is adjacent to the second analysis room R4. The accommodation room R5 is surrounded by the top wall 11, the bottom wall 12, and three adjacent side walls 13 of the box 10, and separated from the second analysis room R4 by the partition wall W4. The accommodation room R5 can be isolated from the second analysis room R4. An installable and removable wall W5 can be arranged in the accommodation room R5. The wall W5 separates a work area of the doctor H1 from an area of the laboratory technician H2.

An access opening 13a4 is formed in the side wall 13, which is one of the side walls 13 surrounding the accommodation room R5 and faces the partition wall W4, to allow the medical staffs H1 and H2 to enter and exit the box 10 and carry equipment in and out of the box 10, and a door 13a5 is arranged in the access opening 13a4 to open and close the access opening 13a4. The door 13a5 may be opened and closed by power such as electricity, or may be manually opened and closed. The door 13a5 has the ability to shield the access opening 13a4. Stairs 13a6 for ascending to and descending from the access opening 13a4 are stowably and deployably or detachably arranged in the access opening 13a4. The accommodation room R5 can be isolated from the outside of the box 10.

Figure 27:
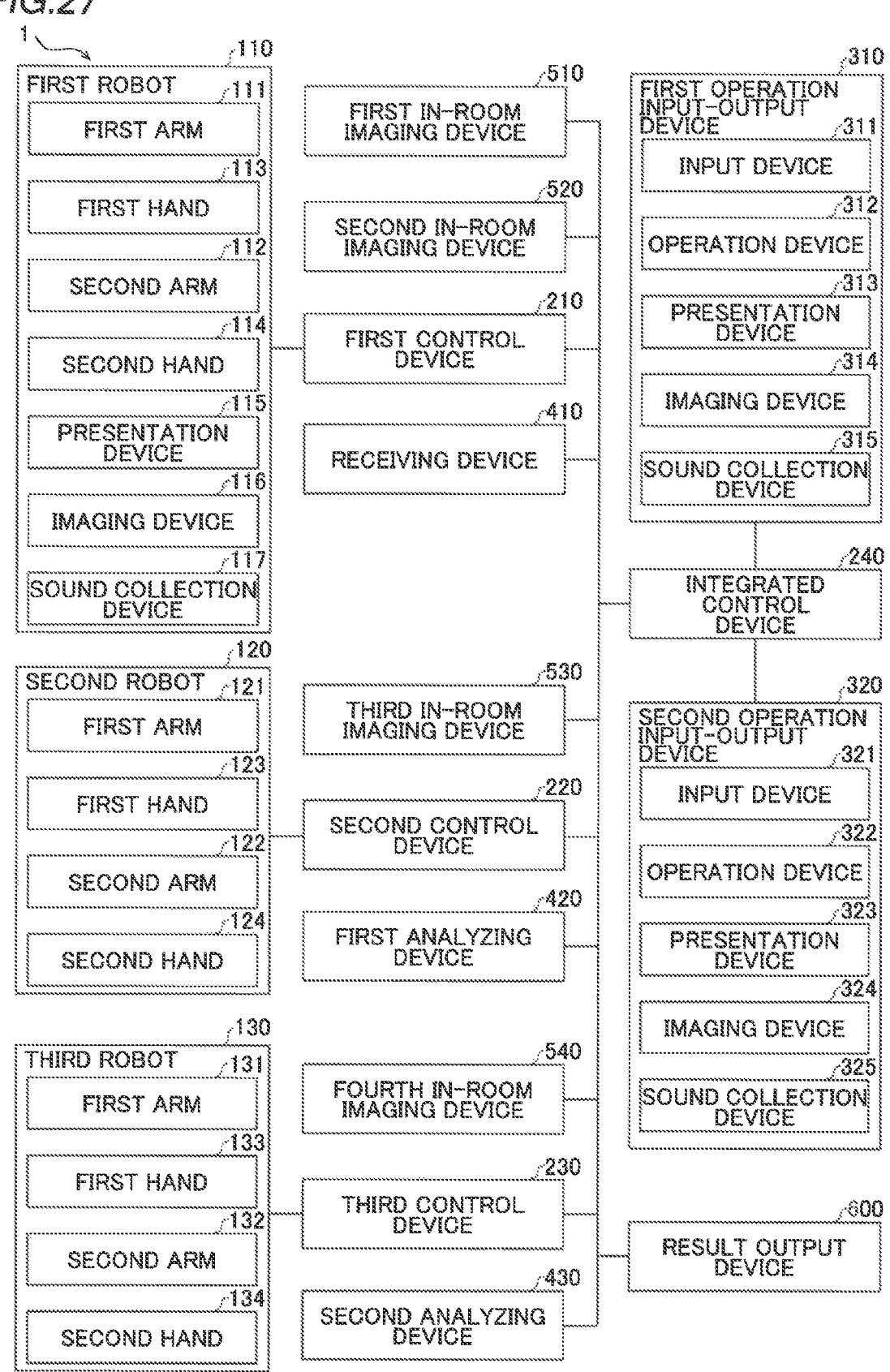
FIG. 27 is a block diagram showing an example of the functional structure of the testing equipment system according to the fourth embodiment.

FIG. 27 is a block diagram showing an example of the functional structure of the testing equipment system 1 according to the fourth embodiment. As shown in FIGS. 25 to 27, the fourth unit portion U4 includes a first in-room imaging device 510 in the examination room R1. The first in-room imaging device 510 includes a visible light camera, for example, and images the inside of the examination room R1. The first in-room imaging device 510 transmits the captured image data to at least one of a presentation device 313 of a first operation input-output device 310 or a presentation device 323 of a second operation input-output device 320 placed in the accommodation room R5.

The first unit portion U1 includes a first air conditioning system AC1 to create a negative pressure environment in the collection room R2. The first air conditioning system AC1 creates a negative pressure environment in the collection room R2 and the examination room R1 communicating with the collection room R2. Thus, the air pressure in the collection room R2 and the examination room R1 is lower than the air pressure in the first analysis room R3. The air pressure in the collection room R2 and the examination room R1 may be lower than the outside air pressure. The first air conditioning system AC1 may include an air conditioner, an air cleaning device, an intake and exhaust device, a duct, a filter, a backflow prevention damper, etc. By the action of the first air conditioning system AC1, leakage of pathogens present in the air to the outside of the collection room R2 and the examination room R1 is reduced or prevented.

The first unit portion U1 includes a first robot 110 that performs an action of collecting the specimen from the subject P, a receiving device 410, and a second in-room imaging device 520 in the collection room R2. The first robot 110 is operated by the operation input-output devices 310 and 320. The first robot 110 includes a communication device such that the doctor H1 who operates the first operation input-output device 310 and the subject P can communicate with each other. The second in-room imaging device 520 includes a visible light camera, for example, and images the inside of the collection room R2. The second in-room imaging device 520 transmits the captured image data to the presentation device 323 of the second operation input-output device 320.

The first unit portion U1 may further include, in the collection room R2, instruments for the first robot 110 to perform medical testing actions, experimental devices, various test reagents, etc. Examples of the instruments include autopipettes, tips used for autopipettes, microtubes, tubes, and centrifuge tubes. Examples of the experimental devices include centrifuges and PCR devices.

The receiving device 410 can receive the specimen from the first robot 110. Although not limited to this, in the fourth embodiment, the receiving device 410 has a function of inactivating the specimen. The receiving device 410 may further have a function of dispensing the specimen, but the first robot 110 may dispense the specimen with the receiving device 410. The receiving device 410 may have a function of transferring the inactivated specimen to the first analysis room R3, but the first robot 110 may transfer the inactivated specimen to the first analysis room R3 through the opening of the shutter W2a.

The first robot 110 performs at least one of an action of collecting the specimen from the subject P, an action of putting the specimen into the receiving device 410, an action of dispensing the specimen with the receiving device 410, an action of taking out the inactivated specimen from the receiving device 410, or an action of transferring the inactivated specimen to the first analysis room R3.

For example, the first robot 110 performs an action of collecting the specimen from the subject P according to an operation by the doctor H1 using the first operation input-output device 310. The doctor H1 manually operates the first robot 110 to collect the specimen, but the first robot 110 may be equipped with AI (artificial intelligence) and automatically operated. The first robot 110 performs the actions other than the action of collecting the specimen according to commands received from the second operation input-output device 320, but may perform the actions according to commands received from the first operation input-output device 310. The first robot 110 is automatically operated according to automation programs to perform the actions other than the action of collecting the specimen, but may be manually operated using the operation input-output device 320 or 310 to perform the actions.

The shutter W2a of the partition wall W2 may be operated by either the operation input-output device 310 or 320, and may be automatically controlled by a first control device 210 or an integrated control device 240.

Figure 28:
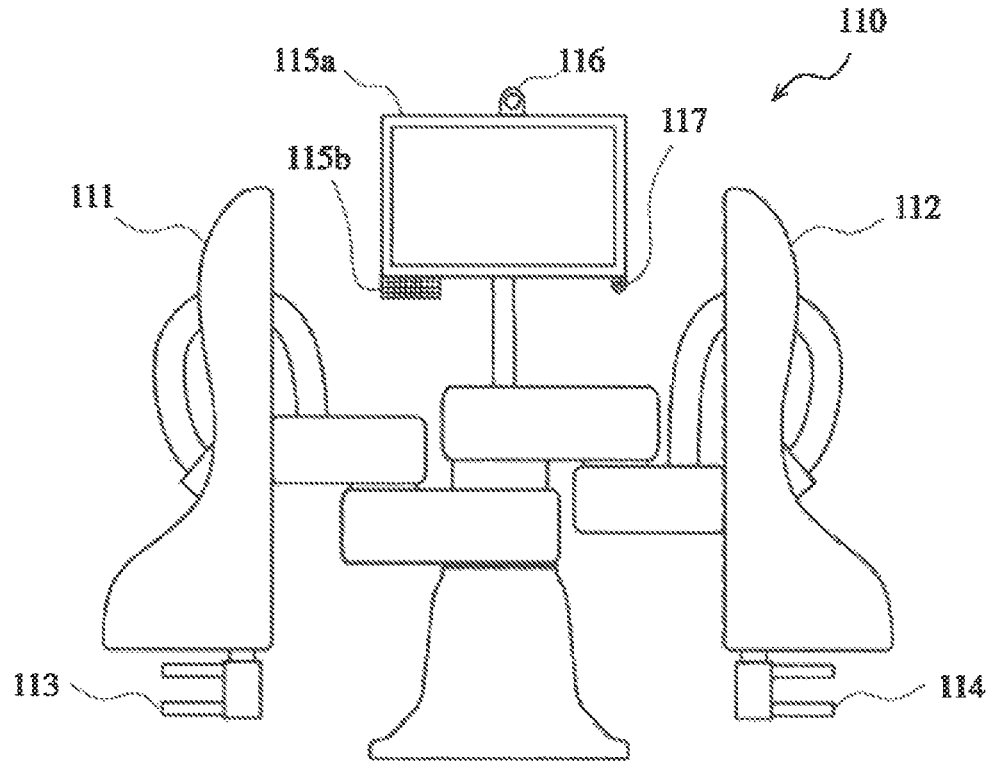
FIG. 28 is a front view showing an example of the structure of a first robot according to the fourth embodiment.

The structure of the first robot 110 is now described. FIG. 28 is a front view showing an example of the structure of the first robot 110 according to the fourth embodiment. As shown in FIG. 28, the first robot 110 includes arms 111 and 112, which are robot arms, and hands 113 and 114, which are robot hands attached to the tip ends of the arms 111 and 112, respectively. The hands 113 and 114 act on objects and are also called end effectors. The arms 111 and 112 are each horizontal articulated robot arms, and the bases of the arms 111 and 112 are arranged coaxially. The first robot 110 is a coaxial dual-arm robot. A second robot 120 and a third robot 130, which are described below, are also coaxial dual-arm robots.

Each of the robots 110 to 130 is not limited to a coaxial dual-arm robot including horizontal articulated robot arms, and may be any robot. For example, the robots 110 to 130 may include any type of robot arm, such as a vertical articulated robot arm, a polar-coordinate robot arm, a cylindrical robot arm, a Cartesian coordinate robot arm, or another type of robot arm. The number of arms of the robots 110 to 130 may be any number of one, or three or more. The robots 110 to 130 have the same structure as an industrial robot, but may have the same structure as a service robot or a humanoid robot, for example. The service robot is a robot used in various service industries such as nursing care, medical care, cleaning, security, guidance, rescue, cooking, and product provision.

The first robot 110 further includes a presentation device 115 (see FIG. 27), an imaging device 116, and a sound collection device 117. The presentation device 115, the imaging device 116, and the sound collection device 117 are devices for communication between the subject P and the doctor H1.

The imaging device 116 includes a visible light camera, for example, images the subject P in the examination room R1 through the partition plate W1a, and transmits the captured image data to at least the first operation input-output device 310 of the first operation input-output device 310 and the second operation input-output device 320. The sound collection device 117 includes a microphone, for example, collects the voice or the like of the subject P in the examination room R1 through the partition plate W1a, and transmits the collected audio signal to at least the first operation input-output device 310 of the first operation input-output device 310 and the second operation input-output device 320.

The presentation device 115 includes a display 115a and an audio output device 115b. The display 115a may be a liquid crystal display, or an organic or inorganic EL display (electro-luminescence display), for example. The audio output device 115b may be a speaker, an earphone, or a headphone, for example. The display 115a and the audio output device 115b present an image and audio corresponding to the image data and the audio signal acquired by an imaging device 314 and a sound collection device 315 (see FIG. 27) of the first operation input-output device 310 to the subject P in the examination room R1 through the partition plate W1a. The display 115a and the audio output device 115b may present an image and audio corresponding to image data and an audio signal acquired by an imaging device 324 and a sound collection device 325 (see FIG. 27) of the second operation input-output device 320 to the subject P.

In the fourth embodiment, the imaging device 116 and the sound collection device 117 are fixedly arranged on the display 115a, but the present disclosure is not limited to this as long as the image and voice of the subject P can be acquired. For example, the imaging device 116 and the sound collection device 117 may be arranged on or in the arms 111 and 112, the partition plate W1a, the subject P, or the examination room R1, for example. The display 115a is fixedly arranged in the vicinity of the bases of the arms 111 and 112 of the first robot 110, but the present disclosure is not limited to this as long as the subject P can be presented with an image. The audio output device 115b is fixedly arranged on the display 115a, but the present disclosure is not limited to this as long as the subject P can be presented with audio. For example, the display 115a and the audio output device 115b may be arranged on or in the arms 111 and 112, the partition plate W1a, the subject P, or the examination room R1, for example.

As shown in FIGS. 25 to 27, the second unit portion U2 includes second air conditioning systems AC2a and AC2b. The second air conditioning system AC2a creates a positive pressure environment in the first analysis room R3, and makes the air pressure in the first analysis room R3 higher than the air pressure in the collection room R2. Thus, the inflow of air from the collection room R2 and the second analysis room R4 to the first analysis room R3 is reduced or prevented. The air pressure in the first analysis room R3 may be higher than the outside air pressure. The second air conditioning system AC2b creates a negative pressure environment in the second analysis room R4, and makes the air pressure in the second analysis room R4 lower than the air pressure in the first analysis room R3. The second air conditioning systems AC2a and AC2b may include air conditioners, air cleaning devices, intake and exhaust devices, ducts, filters, backflow prevention dampers, etc.

The second unit portion U2 includes the second robot 120 that performs a first analysis action on the specimen sent from the collection room R2, a first analyzing device 420, and a third in-room imaging device 530 in the first analysis room R3. Similarly to the first robot 110, the second robot 120 includes arms 121 and 122 and hands 123 and 124 at the tip ends of the respective arms 121 and 122. The second robot 120 does not communicate with the subject P, and thus the second robot 120 does not include a presentation device, an imaging device, or a sound collection device. However, the second robot 120 may include an imaging device as the eyes of the second robot 120. The second robot 120 is operated by the second operation input-output device 320. The third in-room imaging device 530 includes a visible light camera, for example, and images the inside of the first analysis room R3. The third in-room imaging device 530 transmits the captured image data to the presentation device 323 of the second operation input-output device 320.

The first analyzing device 420 includes various devices and instruments necessary for the first analysis of the inactivated specimen. The first analysis is performed in a positive pressure environment. For example, in the case of PCR testing, the first analysis includes steps of extraction of nucleic acids from the specimen, generation and preparation of a PCR reaction solution, addition of controls, sealing, etc. The first analyzing device 420 includes devices and instruments necessary for each step.

The second robot 120 uses the devices and instruments included in the first analyzing device 420 to perform at least one of the steps of the first analysis. The second robot 120 performs an action of transferring, after the first analysis, the specimen to the second analysis room R4 through the opening of the shutter W3a of the partition wall W3. The first analyzing device 420 may transfer the specimen after the first analysis. The second robot 120 performs each action according to a command received from the second operation input-output device 320, but may perform each action according to a command received from the first operation input-output device 310. The second robot 120 is automatically operated according to an automation program to perform each action, but may be manually operated using the operation input-output device 320 or 310 to perform each action.

The second unit portion U2 includes the third robot 130 that performs a second analysis action on the specimen sent from the first analysis room R3, a second analyzing device 430, and a fourth in-room imaging device 540 in the second analysis room R4. The third robot 130 has the same structure as the second robot 120, and includes arms 131 and 132 and hands 133 and 134 at the tip ends of the respective arms 131 and 132. The third robot 130 may include an imaging device as the eyes of the third robot 130. The third robot 130 is operated by the second operation input-output device 320. The fourth in-room imaging device 540 includes a visible light camera, for example, and images the inside of the second analysis room R4. The fourth in-room imaging device 540 transmits the captured image data to the presentation device 323 of the second operation input-output device 320.

The second analyzing device 430 includes various devices and instruments necessary for the second analysis of the specimen that has undergone the first analysis. The second analysis is performed in a negative pressure environment. For example, in the case of PCR testing, the second analysis includes steps of PCR amplification, detection, output of detection result data, etc. The second analyzing device 430 includes devices and instruments necessary for each step.

The third robot 130 uses the devices and instruments included in the second analyzing device 430 to perform at least one of the steps of the second analysis. The third robot 130 may perform an action of transferring, after the second analysis, the specimen to the accommodation room R5 through the opening of the door W4a of the partition wall W4. The third robot 130 performs each action according to a command received from the second operation input-output device 320, but may perform each action according to a command received from the first operation input-output device 310. The third robot 130 is automatically operated according to an automation program to perform each action, but may be manually operated using the operation input-output device 320 or 310 to perform each action.

The third unit portion U3 includes a third air conditioning system AC3. The third air conditioning system AC3 air-conditions the interior of the accommodation room R5. For example, the third air conditioning system AC3 may make the air pressure in the accommodation room R5 higher than the air pressure in the second analysis room R4, and make it equal to the outside air pressure, for example. The third air conditioning system AC3 may include an air conditioner, an air cleaning device, an intake and exhaust device, a duct, a filter, a backflow prevention damper, etc.

The third unit portion U3 includes the first operation input-output device 310, the second operation input-output device 320, and the result output device 600 in the accommodation room R5. The operation input-output devices 310 and 320 include input devices 311 and 321, operation devices 312 and 322, the presentation devices 313 and 323, the imaging devices 314 and 323, and the sound collection devices 315 and 325, respectively.

The input devices 311 and 321 receive inputs of commands, information, data, etc. from the medical staffs H1 and H2. For example, the input devices 311 and 321 may receive commands for automatic actions by automatic operation to be performed by the robots 110 to 130 and output the commands to the integrated control device 240. The input devices 311 and 321 may include known input means such as levers, buttons, touch panels, joysticks, motion capture, cameras, and microphones. For example, the input devices 311 and 321 may include teaching pendants, which are teaching devices, smart devices such as smartphones or tablets, personal computers, and terminal devices such as dedicated terminal devices.

The operation devices 312 and 322 receive inputs of operations for manually operating the robots 110 to 130 from the medical staffs H1 and H2. The operation devices 312 and 322 may output commands corresponding to the operations to the integrated control device 240. The operation devices 312 and 322 may include known input means such as levers, buttons, touch panels, joysticks, motion capture, cameras, or microphones. In the fourth embodiment, the robots 110 to 130 are controlled in a master-slave manner in manual operation, and the operation devices 312 and 322 include master machines. The operation devices 312 and 322 not only output commands for causing the robots 110 to 130 to perform actions according to the input operations, but also provide feedback of forces acting on the hands of the robots 110 to 130 to the medical staffs H1 and H2 who operate the operation devices 312 and 322.

The operation devices 312 and 322 may include release buttons (not shown) that are pressed by the medical staffs H1 and H2 in an emergency (e.g., when the robots 110 to 130 operate abnormally). A command indicating pressing of the release buttons may be associated with a command for releasing a medical testing instrument or a medical examination instrument held by the hand and/or a command for moving the hand away from the subject P, for example.

The presentation device 313 includes a display and audio output device as illustrated for the presentation device 115 of the first robot 110. The presentation device 313 presents an image and audio corresponding to the image data and the audio signal acquired by the imaging device 116 and the sound collection device 117 of the first robot 110 to the doctor H1 or the like. The presentation device 313 can present the image and voice of the subject P. The presentation device 313 may present images corresponding to the image data acquired by the in-room imaging devices 510 to 540.

The presentation device 323 includes at least a display of the display and an audio output device as illustrated for the presentation device 115 of the first robot 110. The presentation device 323 presents images corresponding to the image data acquired by the in-room imaging devices 510 to 540 to the laboratory technician H2 or the like. The presentation device 323 can present an image of each room. The presentation device 323 may present images and audio corresponding to image data and an audio signal acquired by the imaging device 116 and the sound collection device 117 of the first robot 110 and the imaging devices (not shown) of the robots 120 and 130.

The imaging devices 314 and 324 include visible light cameras, for example. The sound collection devices 315 and 325 include microphones, for example. The imaging device 314 and the sound collection device 315 acquire image data and a voice signal of the doctor H1 or the like who is an operator of the first operation input-output device 310 and output them to the presentation device 115 of the first robot 110. The imaging device 314 and the sound collection device 315 enable the image and voice of the doctor H1 to be presented to the subject P. The imaging device 324 and the sound collection device 325 acquire image data and a voice signal of the laboratory technician H2 or the like who is an operator of the second operation input-output device 320 and output them to the presentation device 115 of the first robot 110. The imaging device 324 and the sound collection device 325 enable the image and voice of the laboratory technician H2 to be presented to the subject P.

The result output device 600 is an example of equipment to output an analysis result. The result output device 600 receives detection result data from the second analyzing device 430. The result output device 600 may attach attached data of judgments, observations, certifications, etc. for the detection result data to the data. The result output device 600 may generate the attached data according to a program, or may generate the attached data according to information input by the doctor H1, the laboratory technician H2, and the like. The result output device 600 outputs the detection result data including the attached data as data that the subject P can visually recognize or as paper. For example, the result output device 600 may output a negative certificate of a PCR test as data or paper.

As shown in FIG. 27, the testing equipment system 1 includes the first control device 210, a second control device 220, a third control device 230, and the integrated control device 240 as control devices for controlling the operation of each device.

The first control device 210 controls the operation of each component of the first robot 110. The second control device 220 controls the operation of each component of the second robot 120. The third control device 230 controls the operation of each component of the third robot 130.

The integrated control device 240 controls the entire testing equipment system 1. For example, the integrated control device 240 receives commands from the operation input-output devices 310 and 320 and outputs the commands to devices subject to the commands, or controls the operation of the devices subject to the commands according to the commands. For example, when the target of the commands from the operation input-output devices 310 and 320 is any of the robots 110 to 130, the integrated control device 240 outputs the commands to the control device for controlling the robot among the control devices 210 to 230. The integrated control device 240 enables any of the robots 110 to 130 to be operated by one first operation input-output device 310, and enables any of the robots 110 to 130 to be operated by one second operation input-output device 320.

For example, when the target of the commands from the operation input-output devices 310 and 320 is any of the in-room imaging devices 510 to 540, the receiving device 410, and the analyzing devices 420 and 430, the integrated control device 240 may output the commands to the device, or control the operation of the device according to the commands. The integrated control device 240 enables any of the devices to be operated by one first operation input-output device 310, and enables any of the devices to be operated by one second operation input-output device 320.

The integrated control device 240 may control the operation of the air conditioning systems AC1, AC2a, AC2b, and AC3.

The control devices 210 to 240 include computer devices. Furthermore, the control devices 210 to 240 may include an electric circuit or the like to control power supplied to the robots 110 to 130 and each device. For example, the control devices 210 to 240 may be arranged in the accommodation room R5. Alternatively, the control devices 210 to 230 may be arranged in the robots 110 to 130.

For example, the computer devices of the control devices 210 to 240 include arithmetic units including processors, memories, etc. The arithmetic units transmit and receive commands, information, data, etc. to and from other devices. The arithmetic units input signals from various devices and output control signals to controlled targets. The memories include semiconductor memories such as volatile memories and nonvolatile memories, and storage devices such as hard disks and SSDs (solid state drives). For example, the memories store programs executed by the arithmetic units and various fixed data, for example.

The functions of the arithmetic units may be implemented by a computer system (not shown) including a processor such as a CPU (central processing unit), a volatile memory such as a RAM (random access memory), a non-volatile memory such as a ROM (read-only memory), etc. The computer system may implement the functions of the arithmetic units by having the CPU execute a program recorded in the ROM using the RAM as a work area. Some or all of the functions of the arithmetic units may be implemented by the computer system described above, may be implemented by dedicated hardware circuitry such as an electronic circuit or an integrated circuit, or may be implemented by a combination of the computer system and hardware circuitry described above. Each of the control devices 210 to 240 may perform each process through centralized control by a single computer device, or may perform each process through distributed control by the cooperation of a plurality of computer devices. For example, at least two of the control devices 210 to 240 may be integrated into a single computing device.

For example, each function of the control devices 210 to 240 may be implemented by a microcontroller, an MPU (micro processing unit), an LSI (large scale integration), a system LSI, a PLC (programmable gate array), or a logic circuit, for example. A plurality of functions of each of the control devices 210 to 240 may be integrated into one chip individually, or some or all of the plurality of functions of each of the control devices 210 to 240 may be integrated into one chip. Furthermore, the circuitry may be general-purpose circuitry or dedicated circuitry. As the LSI, a FPGA (field programmable gate array) that can be programmed after LSI production, a reconfigurable processor that can reconfigure the connection and/or setting of circuit cells inside the LSI, or an ASIC (application specific integrated circuit) in which circuits for a plurality of functions are combined into one circuit for a specific application, for example, may be used.

Components included in the testing equipment system 1 shown in FIG. 27 are connected to each other via wired communication or wireless communication. Any type of wired and wireless communication may be used.

Operation of Testing Equipment System

An example of a testing process flow in the testing equipment system 1 according to the fourth embodiment is now described. An example of a testing process flow in the PCR test is described below.

As shown in FIGS. 25 to 27, first, the subject P enters the examination room R1 and sits on a chair so as to face the first robot 110 through the partition plate W1a. The subject P puts the face of the subject P into the opening of the partition plate W1a according to the instruction of the doctor H1 while communicating with the doctor H1 using the image and voice of the doctor H1 output from the presentation device 115 of the first robot 110 and the image and voice of the subject P input to the imaging device 116 and the sound collection device 117.

The doctor H1 manually operates the first robot 110 using the first operation input-output device 310 to move the hand 113 or 114 and collect a specimen from the subject P using the testing instrument held by the hand. After the collection, the doctor H1 switches the operation control of the first robot 110 to automatic operation or makes an input indicating the completion of collection using the first operation input-output device 310. The first operation input-output device 310 transmits a notification of switching to automatic operation, for example, to the second operation input-output device 320.

Upon perceiving the notification via the second operation input-output device 320, the laboratory technician H2 inputs, to the second operation input-output device 320, an instruction to automatically perform the process of the specimen. The laboratory technician H2 monitors the presence or absence of an abnormality by visually recognizing the image of each room displayed on the presentation device 323 of the second operation input-output device 320 when the specimen is automatically processed. The laboratory technician H2 stops the process or switches automatic operation to manual operation, for example, using the second operation input-output device 320 when an abnormality occurs or as necessary.

The integrated control device 240 causes the first robot 110 and the receiving device 410 to automatically perform an action of inputting the specimen into the receiving device 410 by the first robot 110, an action of dispensing the specimen with the receiving device 410 by the first robot 110, an action of inactivating the specimen by the receiving device 410, an action of taking out the inactivated specimen from the receiving device 410 by the first robot 110, and an action of transferring the inactivated specimen to the first analysis room R3 by the first robot 110 in this order.

The integrated control device 240 causes the shutter W2a to open the opening of the partition wall W2 and causes the first robot 110 to insert the specimen into the opening. The integrated control device 240 operates the second robot 120 to receive the specimen inserted into the opening and causes the shutter W2a to close the opening.

Then, the integrated control device 240 causes the second robot 120 to automatically perform each step of the first analysis in order. After the completion of all the steps of the first analysis, the integrated control device 240 causes the shutter W3a to open the opening of the partition wall W3 and causes the second robot 120 to insert the specimen into the opening. The integrated control device 240 operates the third robot 130 to receive the specimen inserted into the opening and causes the shutter W3a to close the opening.

Then, the integrated control device 240 causes the third robot 130 to automatically perform each step of the second analysis in order. After the completion of all the steps of the second analysis, the integrated control device 240 causes the second analyzing device 430 to output the detection result data to the result output device 600. The integrated control device 240 causes the result output device 600 to issue a test result certificate. The laboratory technician H2 gives the subject P the certificate issued by the result output device 600, such as a negative certificate of the PCR test. The result output device 600 may transmit the data of the certificate to another device such as a terminal device of the subject P.

After delivering the specimen from the first robot 110 to the second robot 120, the integrated control device 240 may switch the operation control of the first robot 110 to manual operation, and output a notification of switching or a notification of delivery completion to the first operation input-output device 310. Thus, the doctor H1 can collect a specimen from the next subject P.

As described above, the testing equipment system 1 according to the fourth embodiment can perform a series of processes from specimen collection from the subject P to output of the test result of the specimen at a location at which the testing equipment system 1 is arranged. Furthermore, the testing equipment system 1 can perform the series of processes described above using only the devices arranged in the box 10. In other words, the testing equipment system 1 enables a series of processes to be performed at a location at which the box 10 is placed simply by placing the box 10.

Modified Example 1 of Fourth Embodiment

A modified example 1 of the fourth embodiment is different from the fourth embodiment in that a second unit portion U2 includes a first front room R3a of a first analysis room R3 and a second front room R4a of a second analysis room R4. In the following, the modified example 1 is described with a focus on the points that are different from the fourth embodiment, and description of points that are similar to the fourth embodiment is omitted as appropriate.

Figure 29:
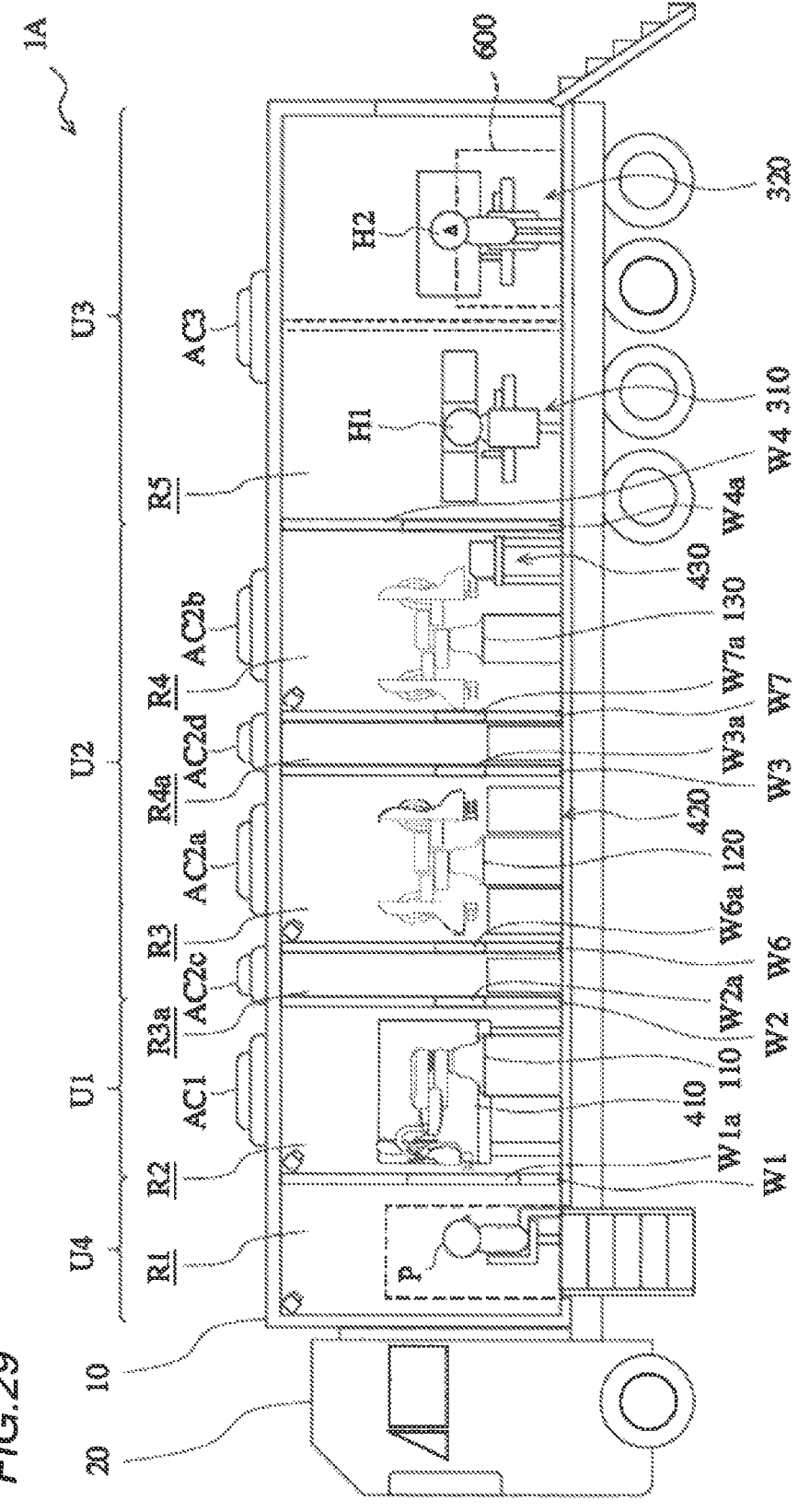
FIG. 29 is a sectional side view showing an example of the structure of a testing equipment system according to a modified example 1 of the fourth embodiment.

FIG. 29 is a sectional side view showing an example of the structure of a testing equipment system 1A according to the modified example 1 of the fourth embodiment. As shown in FIG. 29, the second unit portion U2 of the testing equipment system 1A includes the first front room R3a of the first analysis room R3 and the second front room R4a of the second analysis room R4 in a box 10. The first front room R3a is located between a collection room R2 and the first analysis room R3, and the second front room R4a is located between the first analysis room R3 and the second front room R4a. The second unit portion U2 may include the first front room R3a and the second front room R4a as an analysis unit portion forming the first front room R3a and an analysis unit portion forming the second front room R4a, respectively.

The first front room R3a is separated from the collection room R2 by a partition wall W2, and is separated from the first analysis room R3 by a partition wall W6. Similarly to the partition wall W2, the partition wall W6 includes an opening and a shutter W6a to open and close the opening.

The second front room R4a is separated from the first analysis room R3 by a partition wall W3, and is separated from the second analysis room R4 by a partition wall W7. Similarly to the partition wall W3, the partition wall W7 includes an opening and a shutter W7a to open and close the opening.

The second unit portion U2 includes a second air conditioning system AC2c to adjust the air-conditioned environment of the first front room R3a and a second air conditioning system AC2d to adjust the air-conditioned environment of the second front room R4a. The second air conditioning system AC2c can adjust the air-conditioned environment of the first front room R3a to the same air-conditioned environment as at least the air-conditioned environment of the first analysis room R3 of the air-conditioned environment of the collection room R2 that is a negative pressure environment and the air-conditioned environment of the first analysis room R3 that is a positive pressure environment. The second air conditioning system AC2d can adjust the air-conditioned environment of the second front room R4a to the same air-conditioned environment as at least the air-conditioned environment of the second analysis room R4 of the air-conditioned environment of the first analysis room R3 that is a positive pressure environment and the air-conditioned environment of the second analysis room R4 that is a negative pressure environment.

The integrated control device 240 (see FIG. 27) controls the operation of air conditioning systems AC1, AC2a to AC2d, and AC3.

For example, when the first robot 110 transfers the specimen from the collection room R2, the integrated control device 240 opens a shutter W2a of the partition wall W2 while the first front room R3a is in a positive pressure environment. Then, the integrated control device 240 causes the first robot 110 to place the specimen on a cradle in the first front room R3a, and then closes the shutter W2a. Furthermore, the integrated control device 240 opens the shutter W6a of the partition wall W6 while the first front room R3a is in a negative pressure environment. Then, the integrated control device 240 causes the second robot 120 to transfer the specimen on the cradle in the first front room R3a into the first analysis room R3, and closes the shutter W6a. The first front room R3a may be in a positive pressure environment. Thus, entry of pathogens present in the air from the collection room R2 into the first analysis room R3 is reliably reduced or prevented.

For example, when the second robot 120 transfers the specimen from the first analysis room R3, the integrated control device 240 opens a shutter W3a of the partition wall W3 while the second front room R4a is in a positive pressure environment. Then, the integrated control device 240 causes the second robot 120 to place the specimen on a cradle in the second front room R4a, and then closes the shutter W3a. Furthermore, the integrated control device 240 opens the shutter W7a of the partition wall W7 while the second front room R4a is in a negative pressure environment. Then, the integrated control device 240 causes the third robot 130 to transfer the specimen on the cradle in the second front room R4a into the second analysis room R4, and closes the shutter W7a. Thus, entry of pathogens present in the air from the first analysis room R3 into the second analysis room R4 is reliably reduced or prevented.

In the testing equipment system 1A according to the modified example 1 of the fourth embodiment as described above, movement of pathogens present in the air between the rooms is reliably reduced or prevented.

Modified Example 2 of Fourth Embodiment

A modified example 2 of the fourth embodiment is different from the fourth embodiment in that at least one of a first operation input-output device 310 or a second operation input-output device 320 is arranged at a position away from a box 10. In the following, the modified example 2 is described with a focus on the points different from the fourth embodiment and the modified example 1, and description of points similar to the fourth embodiment and the modified example 1 is omitted as appropriate.

Figure 30:
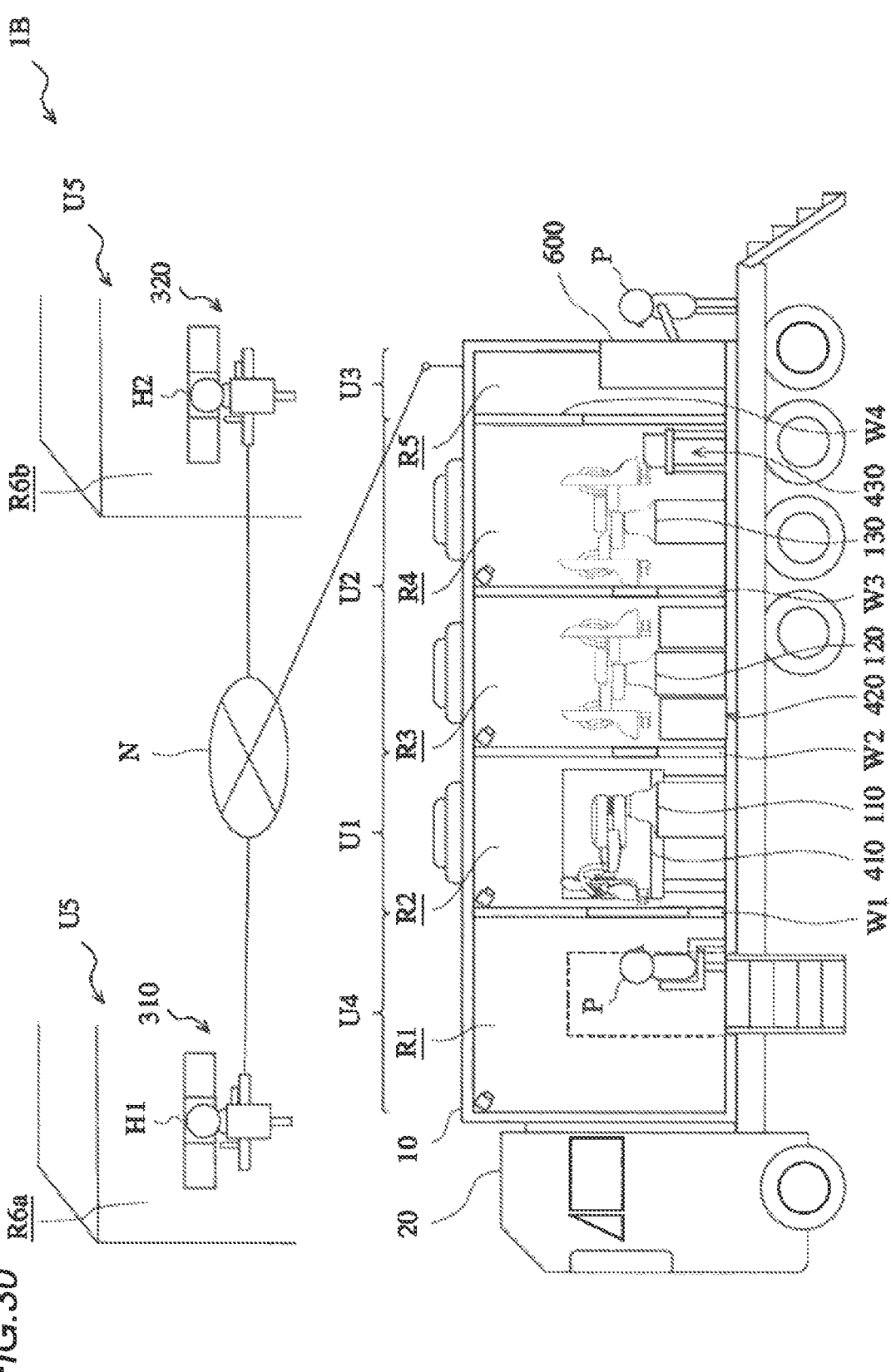
FIG. 30 is a sectional side view showing an example of the structure of a testing equipment system according to a modified example 2 of the fourth embodiment.

FIG. 30 is a sectional side view showing an example of the structure of a testing equipment system 1B according to the modified example 2 of the fourth embodiment. As shown in FIG. 30, in the testing equipment system 1B according to this modified example, a third unit portion U3 does not include the operation input-output devices 310 and 320. The third unit portion U3 includes a result output device 600 in an accommodation room R5, and the result output device 600 can directly output a test result such as a negative certificate to a subject P outside the box 10. In this modified example, the accommodation room R5 does not accommodate medical staffs H1 and H2.

The testing equipment system 1B also includes a fifth unit portion U5 at a position away from the box 10. The fifth unit portion U5 may be arranged at one location or at a plurality of locations. The fifth unit portion U5 includes at least one of the first operation input-output device 310 or the second operation input-output device 320.

In this example, the fifth unit portion U5 is arranged at two locations apart from each other. One fifth unit portion U5 includes an operation room R6a to house the first operation input-output device 310, and the other fifth unit portion U5 includes an operation room R6b to house the second operation input-output device 320. The two fifth unit portions U5 include boxes including the operation rooms R6a and R6b, respectively, and may be arranged together with the boxes or may be arranged in spaces such as rooms in an existing facility, using the spaces as the operation rooms R6a and R6b.

Both the operation input-output devices 310 and 320 communicate with an integrated control device 240 (see FIG. 27) via a communication network N. Therefore, the doctor H1 can remotely operate each device in the box 10 including robots 110 to 130 using the first operation input-output device 310, and the laboratory technician H2 can remotely operate each device in the box 10 including the robots 110 to 130 using the second operation input-output device 320.

The communication network N may be a wired communication network or a wireless communication network. For example, the communication network N may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of a public switched telephone network (PSTN), a mobile phone network, ISDNs (integrated service digital networks), wireless LANs, LTE (Long Term Evolution), CDMA (Code Division Multiple Access), Bluetooth™, satellite communications, etc., or a combination of two or more of these. The communication network N may include one or more networks.

The operation input-output devices 310 and 320 that communicate with the integrated control device 240 (see FIG. 27) via the communication network N may be arranged in the same building or on the same site as the box 10, or may be arranged remotely from these.

The integrated control device 240 (see FIG. 27) of one box 10 may communicate with two or more first operation input-output devices 310 and/or two or more second operation input-output devices 320 via the communication network N. Thus, a plurality of doctors H1 and a plurality of laboratory technicians H2 at various locations can operate each device in the box 10. For example, the plurality of doctors H1 and the plurality of laboratory technicians H2 take turns operating each device such that the testing process can be performed at all hours of the day and night.

In this modified example, the operation input-output devices 310 and 320 communicate with the integrated control device 240 (see FIG. 27) via the communication network N, but may communicate with the integrated control device 240 by wire or wirelessly without going through the communication network N.

In the testing equipment system 1B according to the modified example 2 of the fourth embodiment as described above, there is no need for the doctor H1 and the laboratory technician H2 to reside at a location at which the box 10 is placed. It is possible to reduce the number of doctors H1 and laboratory technicians H2 involved in the testing equipment system 1B.

In this modified example, the operation input-output devices 310 and 320 are arranged in the separate operation rooms R6a and R6b, but the present disclosure is not limited to this. The operation input-output devices 310 and 320 may be arranged in one operation room R6.

A portion of the fifth unit portion U5 may be arranged inside the box 10. That is, one of the operation input-output devices 310 and 320 may be arranged inside the box 10. In this case, a portion of the third unit portion U3 inside the box 10 may also serve as a portion of the fifth unit portion U5.

Example of Arrangement of Testing Equipment System at Airport

Figure 31:
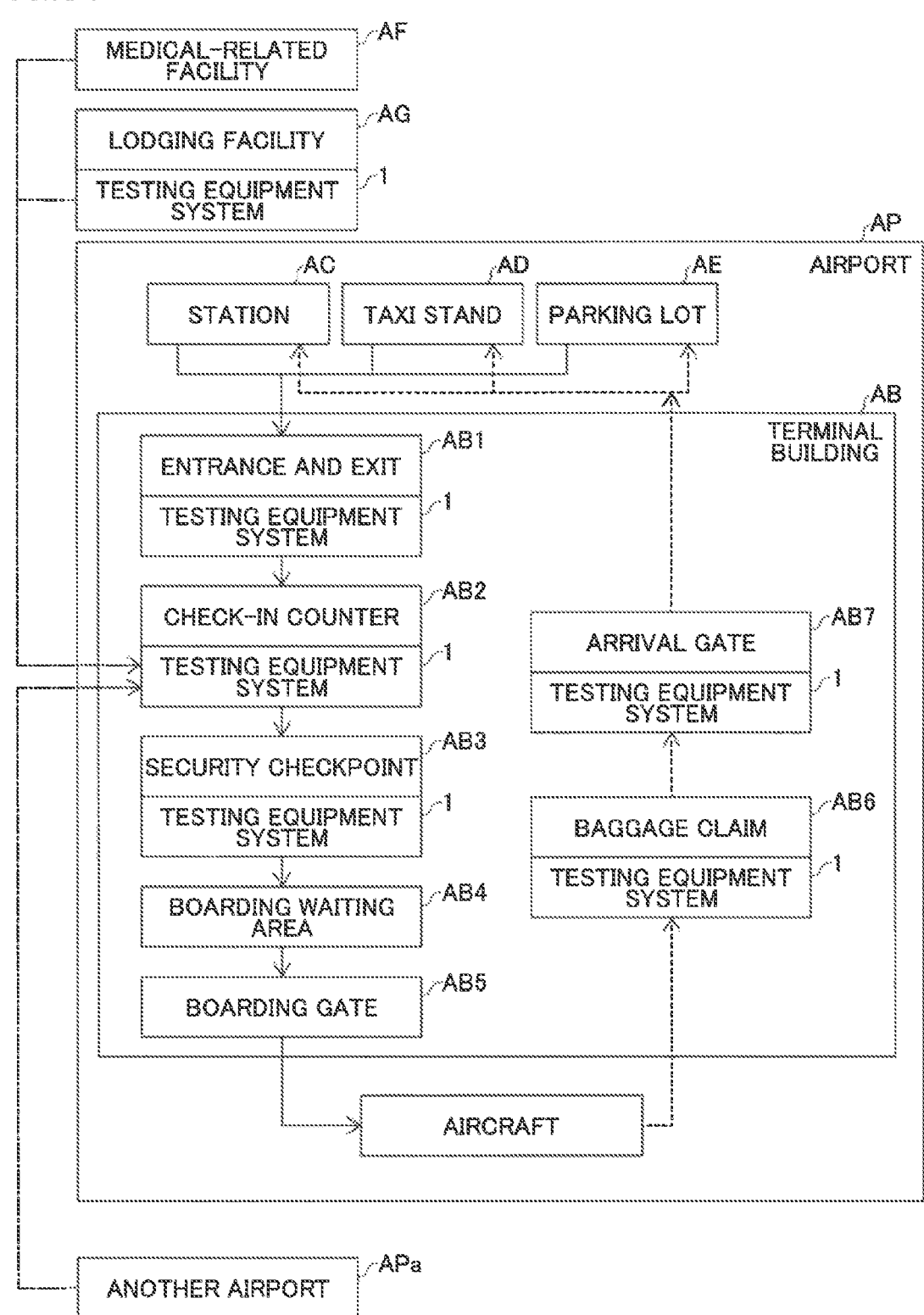
FIG. 31 is a block diagram showing an example of arrangement at an airport of the testing equipment system according to the fourth embodiment.

An example of arrangement of the testing equipment system 1 according to the fourth embodiment is now described. FIG. 31 is a block diagram showing an example of arrangement of the testing equipment system 1 according to the fourth embodiment at the airport AP. In FIG. 31, solid line arrows indicate the flow of passengers of aircraft departing from the airport AP, and dashed line arrows indicate the flow of passengers of aircraft arriving at the airport AP. Dashed-dotted arrows indicate the flow of data communication. As shown in FIG. 31, the airport AP includes a terminal building AB, a railroad and bus station AC, a taxi stand AD, a parking lot AE, etc. The passengers come and go between each of the station AC, the taxi stand AD, and the parking lot AE and an entrance and exit AB1 of the terminal building AB.

The terminal building AB includes the entrance and exit AB1, a check-in counter AB2 for boarding procedures, a security checkpoint AB3 using X-ray inspection and metal detectors or the like, a boarding waiting area AB4, a boarding gate AB5, a baggage claim AB6, and an arrival gate AB7. The passengers of aircraft departing from the airport AP proceed through the check-in counter AB2, the security checkpoint AB3, the boarding waiting area AB4, and the boarding gate AB5 in this order. The passengers of aircraft arriving at the airport AP proceed through the baggage claim AB6 and the arrival gate AB7 in this order.

The box 10 of the testing equipment system 1 is placed at at least one of the entrance and exit AB1, the check-in counter AB2, or the security checkpoint AB3, and in this example, the box 10 is placed at all of them. Thus, passing of untested passengers through the security checkpoint AB3 is reduced or prevented. Furthermore, the box 10 of the testing equipment system 1 is placed at at least one of the baggage claim AB6 or the arrival gate AB7, and in this example, the box 10 is placed at all of them. Thus, passing of untested passengers through the arrival gate AB7 is reduced or prevented.

When there are a plurality of terminal buildings AB, the box 10 of the testing equipment system 1 may be placed at the above locations for each terminal building AB.

The testing equipment system 1 may issue a test result certificate to the passengers or enter test result certificate data into personal belongings of the passengers such as tickets at the location at which the testing equipment system 1 is placed. Alternatively, the testing equipment system 1 may transmit the test result certificate data to another location. The destination may be at least one of the check-in counter AB2, the security checkpoint AB3, or the arrival gate AB7 by which the passengers always drop.

The testing equipment system 1 of the terminal building AB may receive test result certificate data of a person scheduled to be on board who has undergone the test at a facility outside the terminal building AB from the facility via communication. Examples of the outside facility include a medical-related facility AF such as a hospital, a public health center, or a testing facility, a lodging facility AG adjacent to or in the vicinity of the airport AP, and another airport APa from which the passengers have departed. The medical-related facility AF and the lodging facility AG may be located within or outside the grounds of the airport AP.

When the outside facility does not have the testing equipment, the testing equipment system 1 may be placed at the outside facility and may transmit data to the testing equipment system 1 in the terminal building AB. In FIG. 31, the data is transmitted to the testing equipment system 1 at the check-in counter AB2, but it may be transmitted to another testing equipment system 1. The testing equipment system 1 in the terminal building AB may evaluate the credibility of certificates issued from the outside facility based on information on the timing and the implementing agency of testing, for example, and issue a credible certificate as its own certificate. Thus, it is possible to reduce the waiting time of the passengers.

The box 10 of the testing equipment system 1 may be placed not only in the terminal building AB, but also at the station AC, the taxi stand AD, and the parking lot AE. The testing equipment system 1 placed in or at the terminal building AB, the station AC, the taxi stand AD, the parking lot AE, the outside facility, etc. does not necessarily have to include the box 10, and may placed using an existing facility.

Other Embodiments

Although examples of the first to fourth embodiments of the present disclosure have been described, the present disclosure is not limited to the first to fourth embodiments and modified examples described above. That is, various modifications and improvements are possible within the scope of the present disclosure. For example, various modifications with respect to the embodiments and modified examples and modes configured by the combination of components in different embodiments and modified examples are also included in the scope of the present disclosure.

For example, while each unit portion of the testing equipment system is loaded on the mobile body 20 in the first embodiment and modified examples, the present disclosure is not limited to this. Each unit portion of the testing equipment system may be placed at an intended location without being loaded on the mobile body 20. In this case, each unit portion of the testing equipment system can be relocated by a machine, and each transported unit portion may be placed at the intended location by a machine. Each unit portion of the testing equipment system can be assembled in the field, and may be assembled at the intended location. In this case, each unit portion of the testing equipment system may not be housed in the box 10. Each unit portion may be surrounded by walls, ceilings, etc. assembled at the intended location and isolated from the outside, or may be isolated from the outside using the existing walls, ceilings, etc. at the intended location.

While all unit portions of the testing equipment system are integral and unitary with each other and housed in the box 10 as a single unit in the first embodiment and modified examples, the present disclosure is not limited to this. Some or all of the unit portions may be separable. For example, at least one of the unit portions may form one unit, and the one unit may be housed in one box. Furthermore, rooms such as the first analysis room R3 and the second analysis room R4 may be separable. For example, one room may be housed in one box. Such a testing equipment system may include a plurality of boxes.

The plurality of boxes may be spaced apart from each other, or may be connected to each other. One unit and one room formed by at least one of the unit portions may be assemblable at an installation location. In this case, one unit and one room may be surrounded by walls, ceilings, etc. assembled at the installation location and isolated from the outside, or may be isolated from the outside using the existing walls, ceilings, etc. at the installation location.

While a container is illustrated as the box 10 in the first embodiment and modified examples, the structure of the box 10 is not limited to this. The box 10 may have any structure as long as the box 10 can isolate the interior space of the box 10 from the exterior space. For example, the box 10 may be a unit house or the like that is assembled in advance into a box shape or that can be assembled on the mobile body 20 or the like.

While the processes in the collection room R2, the first analysis room R3, and the second analysis room R4 are performed by the robots 110 to 130 in the first embodiment and modified examples, the present disclosure is not limited to this. The process in at least one of the three rooms may be performed by a medical staff.

While the robots 110 to 130 arranged in the collection room R2, the first analysis room R3, and the second analysis room R4 are of the same type in the first embodiment and modified examples, the present disclosure is not limited to this. The robots 110 to 130 may be of different types. The arranged robots may be robots suitable for the process in each room.

While the testing equipment system includes the first unit portion U1 to the fourth unit portion U4 in the first embodiment and modified examples, the present disclosure is not limited to this. The testing equipment system may further include another unit portion and may not include at least one of the first to fourth unit portions U1 to U4. For example, the testing equipment system may not include the fourth unit portion U4 including the examination room R1. For example, when the testing equipment system is placed outdoors, the testing equipment system may collect a specimen from the subject P outside the box 10.

While the testing equipment system is placed at at least one of a starting point or an end point of movement across a geographical boundary in the first embodiment and modified examples, the present disclosure is not limited to this. For example, the testing equipment system may be placed at a location at which many people gather or at which people who are likely to carry pathogens gather. For example, the testing equipment system may be placed in a hospital, a health center, a PCR testing facility, a lodging facility, an isolation facility for pathogen carriers, a large building, a stadium, and a hall. In this case, each unit portion of the testing equipment system may be placed in a state of being housed in a box, or may be placed using a facility such as a room at an installation location.

Examples of aspects of the technology of the present disclosure include the following. A testing equipment system according to an aspect of the present disclosure collects and analyzes a specimen from a subject, and includes a first unit portion forming a collection room including equipment to collect the specimen, a second unit portion forming an analysis room including equipment to analyze the specimen separately from the collection room, and a third unit portion including equipment to output an analysis result. The testing equipment system can be placed at at least one of a starting point or an end point of movement across a geographical boundary.

According to the aforementioned aspect, the testing equipment system includes the first unit portion to collect the specimen, the second unit portion to analyze the specimen, and the third unit portion to output the analysis result. The testing equipment system enables a series of processes including specimen collection, specimen analysis, and test result output at a location at which the testing equipment system is placed. The first unit portion forms the collection room, and the second unit portion forms the analysis room. The testing equipment system including such a first unit portion and a second unit portion can be easily placed even at a location without testing equipment. The testing equipment system can simplify establishment of an environment in which testing is possible at a location without testing equipment.

In a testing equipment system according to one aspect of the present disclosure, a first unit portion may include a first air conditioning system to create a negative pressure environment in a collection room.

According to the aforementioned aspect, the first air conditioning system can reduce or prevent the spread of pathogens and the like contained in a specimen and subject's droplets to the outside of the collection room, and can provide an air-conditioned environment suitable for the collection room. The first unit portion includes the first air conditioning system, and thus the first air conditioning system is easily placed.

In a testing equipment system according to one aspect of the present disclosure, a second unit portion may include a second air conditioning system to create a positive pressure environment or a negative pressure environment in an analysis room.

According to the aforementioned aspect, the second air conditioning system can provide an air-conditioned environment suitable for the analysis room. The second unit portion includes the second air conditioning system, and thus the second air conditioning system is easily placed.

A testing equipment system according to an aspect of the present disclosure may further include a fourth unit portion forming an examination room to examine a subject to collect a specimen from the subject, separately from an analysis room.

According to the aforementioned aspect, the testing equipment system eliminates the need for a separate examination room from the testing equipment system. The testing equipment system enables a series of processes including examination, specimen collection, and specimen analysis at a location at which the testing equipment system is placed.

In a testing equipment system according to one aspect of the present disclosure, a third unit portion may form an accommodation room to accommodate a medical staff, separately from a collection room.

According to the aforementioned aspect, the testing equipment system eliminates the need for a separate accommodation room for accommodating a medical staff from the testing equipment system. The testing equipment system allows the medical staff to do their job at a location at which the testing equipment system is placed. For example, the job may include evaluating an analysis result and issuing a certificate of the analysis result. Furthermore, the accommodation room is separated from the collection room, and thus contamination of a medical staff with pathogens is prevented.

In a testing equipment system according to one aspect of the present disclosure, at least one of a first unit portion or a second unit portion may include a robot capable of performing at least one of an action for specimen collection or an action for specimen analysis. Furthermore, the first unit portion may include a robot capable of performing an action for specimen collection.

According to the aforementioned aspect, substitution of a robot for specimen collection and/or specimen analysis is possible. Thus, the number of medical staffs involved in specimen collection and specimen analysis can be reduced. Robotic automation enables continuous processing regardless of time. In addition, substitution of a robot for specimen collection can reduce the risk of contamination of a medical staff with pathogens.

A testing equipment system according to one aspect of the present disclosure may further include an operator placed in an accommodation room formed by a third unit portion to operate a robot, and the accommodation room may be formed separately from a collection room, and may accommodate a medical staff.

According to the aforementioned aspect, the medical staff can operate the robot using the operator in the accommodation room separated from the collection room. Thus, exposure of the medical staff to pathogens is reduced.

A testing equipment system according to one aspect of the present disclosure may further include an operator placed at a remote location away from all of unit portions including robots to remotely operate the robots via a communicator.

According to the aforementioned aspect, a medical staff can remotely operate the robots using the operator at the remote location away from all of the unit portions including the robots. For example, even when the medical staff is not at a location at which the testing equipment system is placed, processing by the testing equipment system is possible. For example, the medical staff can remotely operate robots even for a plurality of testing equipment systems placed at a plurality of locations away from each other. Therefore, it is possible to operate the testing equipment system with fewer medical staffs.

In a testing equipment system according to one aspect of the present disclosure, at least one of unit portions may form a separate unit separable from the remaining unit portions.

According to the aforementioned aspect, it is possible to change the arrangement of the unit portions. For example, it is possible to arrange the unit portions according to the environment of a location at which the testing equipment system is placed.

In a testing equipment system according to one aspect of the present disclosure, unit portions may be integral and unitary with each other to form one unit.

According to the aforementioned aspect, it is possible to collectively handle all of the unit portions provided in the testing equipment system. All of the unit portions provided in the testing equipment system are integral and unitary with each other, and thus it is possible to downsize the testing equipment system and to simplify the structure of the testing equipment system.

In a testing equipment system according to one aspect of the present disclosure, one unit may include one box to house the entirety of unit portions.

According to the aforementioned aspect, all of the unit portions provided in the testing equipment system are integrated in one box. Thus, placement and removal of the testing equipment system is simplified.

In a testing equipment system according to one aspect of the present disclosure, a unit formed by unit portions may be relocatable by a machine.

According to the aforementioned aspect, placement and removal of the unit is simplified.

In a testing equipment system according to one aspect of the present disclosure, a unit formed by unit portions may be loadable on a mobile body.

According to the aforementioned aspect, it is possible to move the unit using the mobile body. Therefore, it is possible to easily place the unit at various locations.

In a testing equipment system according to one aspect of the present disclosure, a unit formed by unit portions may be a ready-to-assemble unit that is assembled at an installation location.

According to the aforementioned aspect, it is possible to place the unit according to the environment of a location at which the testing equipment system is placed. For example, even when the assembled unit cannot be carried into the installation location, the unit can be placed.

In a testing equipment system according to one aspect of the present disclosure, a second unit portion may include a first analysis unit portion forming a first analysis room including equipment to perform a first analysis on a specimen, separately from a collection room, and a second analysis unit portion forming a second analysis room including equipment to perform a second analysis on the specimen, separately from the collection room and the first analysis room. The first analysis unit portion may include an air conditioning system to create one of a positive pressure environment and a negative pressure environment in the first analysis room as a second air conditioning system, and the second analysis unit portion may include an air conditioning system to create the other of the positive pressure environment and the negative pressure environment in the second analysis room as the second air conditioning system.

According to the aforementioned aspect, the testing equipment system can include a plurality of analysis rooms with different air conditioning environments. Therefore, the testing equipment system can accommodate analysis of various specimens.

A testing equipment system according to one aspect of the present disclosure may be placed in an airport terminal building.

According to the aforementioned aspect, the testing equipment system enables testing of passengers who board the aircraft and depart from the airport before departure and output of the results to the passengers, and enables testing of passengers who have boarded the aircraft and arrived at the airport before leaving the airport and output of the results to the passengers. The test results prove the presence or absence of contamination of the passengers. Therefore, the spread of pathogens by people infected with pathogens to other areas such as other countries is reduced or prevented. In addition, the possibility that uninfected people cannot fly to other areas is reduced or prevented.

In a testing equipment system according to one aspect of the present disclosure, a specimen may be a specimen subjected to a PCR (polymerase chain reaction) test, and analysis may be performed for the PCR test.

According to the aforementioned aspect, the testing equipment system can establish an environment in which the PCR test is possible at a location without testing equipment for the PCR test.

Note that all the numbers used above, such as the order and the quantity, are illustrated in order to concretely explain the technique of the present disclosure, and the present disclosure is not limited to the illustrated numbers. Furthermore, the connection relationships between the components are illustrated in order to concretely explain the technique of the present disclosure, and the connection relationship that realizes the functions of the present disclosure is not limited to those relationships.

DESCRIPTION OF REFERENCE NUMERALS

1, 1A, 1B: testing equipment system
20: mobile body
110, 120, 130: robot
1001: first unit
1002, 1002*a*: second unit
1003: third unit
1004: robot
1004*a*, 1004*b*: first robot
1004*c*: second robot
1004*d*: third robot
1004*g*: fourth robot
1005: container
1006*a*, 1006*b*: conveyance section
1007*a*: specimen collection container
1007*b*: plate
1007*c*: multiple-connected tube
1011: subject area
1012: robot area
1013: specimen collection container conveyance section
1014: scale
1015: disinfectant bath
1017*a*: ultraviolet irradiator
1017*b*: sterilizer
1018: first centrifuge
1019: shaker
1021: cabinet
1022: storage rack (storage)
1025: magnet portion
1029: disposal box
1031: reagent preparation room
1032: measurement room
1034: specimen measurement unit
1034*a*: open state detector
1036: tube holder
1063: plate conveyance section
1073: well
1100, 1300: testing system
1113: notifier
1121: air conditioner
1181: imager
1241: chute
1311: shutter
1511: moving robot
1541: dispensing robot
P: subject
U1: first unit portion
U2: second unit portion
U3: third unit portion
U4: fourth unit portion
U5: fifth unit portion

The invention claimed is:

1. A testing system to collect a specimen from a subject to perform measurement to complete testing of the specimen, the testing system comprising:

a box comprising a freight container provided on a mobile body, the box comprising an integrated plurality of unit portions arranged in a row and configured to allow: specimen collection by a first robot of a first processing unit for collecting and receiving the specimen; preprocessing for processing the collected specimen before measurement by a second robot of a second processing unit; and specimen measurement by a third robot of a third processing unit for measuring the preprocessed specimen, the specimen collection, preprocessing and specimen measurement to be performed within the integrated plurality of unit portions; wherein the integrated plurality of unit portions comprises:

a first unit portion in which the first robot is configured to perform the specimen collection from the subject;

a second unit portion connected to the first unit portion, and in which the third robot is configured to perform measurement of the preprocessed specimen;

a third unit portion connected to the second unit and configured to perform output of the results of the measurement of the preprocessed specimen;

a fourth unit portion forming an examination room, the examination room provided for examining the subject to collect the specimen from the subject, the fourth unit portion provided separately from the first, second, and third unit portions so as to prevent or reduce entry of pathogens present in the air; and a conveyance section to connect the first processing unit, the second processing unit, and the third processing unit to each other and to facilitate movement of the specimen between the first processing unit, the second processing unit, and the third processing unit, wherein the second processing unit is located in either the first unit portion or the second unit portion, the fourth unit portion is positioned adjacent to the first unit portion such that the first robot is configured to open a door to an access opening and collect the specimen from the subject in the fourth unit portion through the access opening and place the collected specimen on the conveyance section, the conveyance section enables:

the specimen collected from the subject by the first robot in the first processing unit through the access opening and placed on the conveyance section, to be transferred to the second processing unit, the specimen transferred by the conveyance section from the first processing unit to the second processing unit to be picked from the conveyance section in the second processing unit by the second robot and preprocessed therein, and placed on the conveyance section and transferred to the third processing unit, and the preprocessed specimen transferred by the conveyance section from the second processing unit to the third processing unit to be picked from the conveyance section in the third processing unit by the third robot and measured therein.

2. The testing system according to claim 1, placed at a moving base for getting on and off a mobile body.

3. The testing system according to claim 1, wherein the first processing unit is operable to collect and receive a saliva or nasal specimen.

4. The testing system according to claim 1, wherein the first processing unit includes a first robot corresponding to the robot operable to process the specimen; and the first robot is operable to sterilize an inside of the first unit portion including the first processing unit with an ultraviolet irradiator.

5. The testing system according to claim 4, wherein the first processing unit further includes a disinfectant bath to disinfect an outer surface of a specimen collection container containing the collected specimen.

6. The testing system according to claim 4, wherein the first unit portion further includes a subject area in which at least a portion of subject is placed through the access opening, a robot area in which the first robot, the robot area being partitioned from the subject area, and a specimen collection container conveyance section to transport a specimen collection container containing the collected specimen from the subject area to the robot area.

7. The testing system according to claim 6, wherein the first unit portion further includes an air conditioner to adjust an air flow in the subject area.

8. The testing system according to claim 4, wherein the first processing unit further includes a sterilizer to sterilize the first robot operable to collect the specimen.

9. The testing system according to claim 1, wherein the second robot is configured to dispense a diluted specimen onto a plate having a plurality of wells; and the second processing unit includes a plate conveyance section to transport the plate over a predetermined period of time to inactivate the specimen on the plate.

10. The testing system according to claim 9, wherein the second processing unit further includes a storage including a first placement section to store, for a predetermined period of time, a specimen collection container containing the collected specimen, from which a portion of the specimen has been dispensed onto the plate and in which a remaining portion of the specimen has been contained.

11. The testing system according to claim 10, wherein the second robot comprises a moving robot configured to move the specimen collection container into the storage.

12. The testing system according to claim 10, wherein the storage is provided between a dispenser to dispense the specimen and a centrifuge to perform centrifugal separation.

13. The testing system according to claim 10, wherein the storage includes a second placement section on which the specimen collection container is placed before the specimen is dispensed from the specimen collection container.

14. The testing system according to claim 9, wherein the second processing unit further includes:

a cabinet having an interior space in which the diluted specimen is dispensed onto the plate by the second robot;

a chute to discard a tip for dispensing the diluted specimen; and a third robot, as the robot, to supply the plate to a dispensing position.

15. The testing system according to claim 9, wherein the second robot comprises a dispensing robot configured to dispense a reagent onto the plate.

16. The testing system according to claim 1, wherein the third processing unit includes:

a reagent preparation room to prepare a reagent for measuring the specimen;

a measurement room to measure the specimen; and an open state detector to detect that a lid of a multiple-connected tube including a row of tubes operable to accommodate a plurality of specimens to be measured is open;

the reagent preparation room is under a positive pressure; and the measurement room is under a negative pressure.

17. The testing system according to claim 1, wherein the third processing unit is operable to measure the specimen by a PCR (polymerase chain reaction) test.

18. The testing system according to claim 1, wherein the third robot comprises a fourth robot configured to perform processing to measure the specimen.

* * * * *